US008669231B2

(12) United States Patent
Denmeade et al.

(10) Patent No.: US 8,669,231 B2
(45) Date of Patent: *Mar. 11, 2014

(54) ACTIVATION OF PEPTIDE PRODRUGS BY HK2

(75) Inventors: Samuel R. Denmeade, Ellicot City, MD (US); John Tod Isaacs, Pheonix, MD (US); Hans Lilja, Skanor (SE)

(73) Assignee: GenSpera, Inc., San Antonio, TX (US)

( * ) Notice: Subject to any disclaimer, the term of this patent is extended or adjusted under 35 U.S.C. 154(b) by 147 days.

This patent is subject to a terminal disclaimer.

(21) Appl. No.: 12/987,409

(22) Filed: Jan. 10, 2011

(65) Prior Publication Data

US 2011/0245147 A1 Oct. 6, 2011

Related U.S. Application Data

(62) Division of application No. 10/535,351, filed as application No. PCT/US03/36880 on Nov. 18, 2003, now Pat. No. 7,906,477.

(60) Provisional application No. 60/427,309, filed on Nov. 18, 2002.

(51) Int. Cl.
| | |
|---|---|
| *A61P 35/00* | (2006.01) |
| *A61K 38/08* | (2006.01) |
| *A61K 38/04* | (2006.01) |
| *A61K 38/00* | (2006.01) |
| *C07K 7/06* | (2006.01) |
| *A61K 47/42* | (2006.01) |
| *C07K 1/00* | (2006.01) |

(52) U.S. Cl.
USPC ........... 514/19.5; 514/1.3; 514/21.6; 514/1.1; 530/329; 530/333; 530/344; 530/345

(58) Field of Classification Search
None
See application file for complete search history.

(56) References Cited

U.S. PATENT DOCUMENTS

| | | | | |
|---|---|---|---|---|
| 5,516,639 | A * | 5/1996 | Tindall et al. | 435/7.4 |
| 6,410,514 | B1 * | 6/2002 | Isaacs et al. | 514/1.3 |
| 6,545,131 | B1 * | 4/2003 | Isaacs et al. | 530/391.7 |
| 7,635,682 | B2 * | 12/2009 | Denmeade et al. | 514/1.1 |
| 7,906,477 | B2 * | 3/2011 | Denmeade et al. | 514/1.1 |
| 2008/0247950 | A1 * | 10/2008 | Denmeade et al. | 424/9.1 |
| 2011/0245147 | A1 * | 10/2011 | Denmeade et al. | 514/1.3 |

OTHER PUBLICATIONS

Vander Griend, D., et at., Amino acid containing thapsigargin analogues deplete androgen receptor protein via synthesis inhibition and induce the death of prostate cancer cells, Mol Cancer Ther 2009;8(5).
Janssen, S., et al., Pharmacokinetics, Biodistribution, and Antitumor Efficacy of a Human Glandular Kallikrein 2 (hK2)-Activated Thapsigargin Prodrug, The Prostate 66:358-368 (2006).
Janssen, et al., Screening a combinatorial peptide library to develop a human glandular kallikrein 2-activated prodrug as targeted therapy for prostate cancer. Mol Cancer Ther 2004;3:1439-1450.

* cited by examiner

*Primary Examiner* — Maury Audet
(74) *Attorney, Agent, or Firm* — Logue, PLLC

(57) ABSTRACT

The invention provides novel peptide prodrugs that contain cleavage sites specifically cleaved by human kallikrein 2 (hK2). These prodrugs are useful for substantially inhibiting the non-specific toxicity of a variety of therapeutic drugs. Upon cleavage of the prodrug by hK2, the therapeutic drugs are activated and exert their toxicity. Methods for treating cell proliferative disorders are also featured in the invention.

7 Claims, 9 Drawing Sheets

Table 1. Amino acid sequence of peptides hydrolyzed by human glandular kallikrein2 (hK2)

| | | | | | | |
|---|---|---|---|---|---|---|
| G | K | A | R/ | A | F | (SEQ ID NO: 1) |
| G | K | A | V | R/ | Q | (SEQ ID NO: 2) |
| G | K | A | Y | F | M/ | (SEQ ID NO: 3) |
| G | K | A | E | K | V/ | (SEQ ID NO: 4) |
| G | K | A | F | R// | K/ | (SEQ ID NO: 5) |
| G | K | A | K | P | R/ | (SEQ ID NO: 6) |
| G | K | A | A | Y | Y/ | (SEQ ID NO: 7) |
| G | K | A | W | Y | H/ | (SEQ ID NO: 8) |
| G | K | A | F | R/ | R// | (SEQ ID NO: 9) |
| G | K | A | I | Q | R/ | (SEQ ID NO: 10) |
| G | K | A | M | R/ | Q// | (SEQ ID NO: 11) |
| G | K | A | A | L | M/ | (SEQ ID NO: 12) |
| G | K | A | Q | G | F/ | (SEQ ID NO: 13) |
| G | K | A | N | M | N/ | (SEQ ID NO: 14) |

Random library constructed with sequence
$NO_2$-Y-G-K-A-X1-X2-X3-Dap-F-K(ABZ)
Where $NO_2$-Y is nitrotyrosine quencher;
X1-X2-X3 are random amino acids consisting
of all natural L-amino acids except cysteine (n=19),
Dap is diaminopropanoate, K(ABZ) is lysine coupled to
fluorophore aminobenzoic acid (ABZ)
HK2 cleavage sites denoted by single or double //

FIG. 1

HPLC ananlysis of hydrolysis of hK2 prodrug Ac-GKAFRR-L12ADT by hK2 (4μg/ml) over 24 hr. incubated in 50 mM TRIS, 0.1 M NaCL, pH 7.8 at room temperature. Mass of each peak confirmed by MALDI-TOF mass spectrometric analysis (see figure 3 for mass-profiles).

HPLC analysis of Ac-GKAFRR-L12ADT incubated in 50% human plasma for 24 hrs at room temperature. Peak 1 represents unidentified plasma contaminant that was also present in control plasma. Peak 2 and 3 both represent Ac-GKAFRR-L12ADT as confirmed by MALDI-TOF mass spectrometric analysis

ACTIVATION OF PEPTIDE PRODRUGS BY HK2

RELATED APPLICATIONS

This application is a divisional application of U.S. application Ser. No. 10/535,351, filed on Apr. 14, 2006, which is a national phase application under 35 U.S.C. §371 of International Application No. PCT/US03/36880, filed on Nov. 18, 2003, which claims the benefit of U.S. Provisional Application No. 60/427,309, filed Nov. 18, 2002, the entire contents of each of which is hereby incorporated by reference.

FIELD OF THE INVENTION

This invention relates generally to the targeted activation of biologically active materials to cells that produce human glandular kallikrein (hK2) and more specifically to hK2-specific peptide substrates that can act as drug carriers. In addition it relates to prodrugs consisting of a peptide covalently coupled to a cytotoxic drug such that the peptide-drug bond can be hydrolyzed by hK2. The coupling of the peptide to the cytotoxic drug creates an inactive prodrug that can only become activated at sites where enzymatically active hK2 is being produced.

BACKGROUND OF THE INVENTION

There is currently no effective therapy for men with metastatic prostate cancer who relapse after androgen ablation, even though numerous agents have been tested over the past thirty years. Prolonged administration of effective concentrations of standard chemotherapeutic agents is usually not possible because of dose-limiting systemic toxicities.

Human Glandular Kallikrein 2 (hK2) is the protein product of the human kallikrein gene hKLK2, one of three related kallikrein genes that also include hKLK1 and hKLK3. These three genes are clustered on chromosome 19q13.2-q13.4. The protein product of hKLK3 is prostate-specific antigen (PSA). While PSA is the predominant tissue kallikrein in the prostate, hK2 is also found almost exclusively in the prostate. hK2 is a glycoprotein containing 237 amino acids and a mass of 28.5 kDa. hK2 and PSA share some properties such as high amino acid sequence identity, prostate localization, androgen regulation and gene expression, but are quite distinct form one another biochemically.

hK2 and PSA differ most markedly in their enzyme properties. Unlike PSA, a chymotrypsin-like protease, hK2 displays the trypsin-like specificity common to most members of the kallikrein family of proteases. hK2 can cleave semenogelin proteins, with an activity that is comparable to PSA. The level of hK2 in the seminal fluid is only 1% of the level of PSA. hK2 has trypsin-like activity, similar to hK1, although it does not appear to function as a classic kininogenase.

In the normal prostate, the levels of expressed hK2 protein are lower than those of PSA. However, hK2 is more highly expressed by prostate cancer cells than by normal prostate epithelium. Comparison of immunohistochemical staining patterns demonstrated incrementally increased staining in poorly differentiated prostate cancers. The intensity of staining has been found to increase with increasing Gleason score, in contrast to PSA, which tends to show decreased staining with increasing Gleason grade, suggesting that hK2 might potentially be a better tumor marker for prostate cancer than PSA.

Recently, three independent groups reported that recombinant hK2 could convert inactive pro-PSA in to the mature PSA protease by release of the propeptide in vitro, thus establishing a possible physiologic connection between hK2 and PSA. hK2 is also secreted in an inactive precursor form. Pro-hK2 may have autocatalytic activity, but the mechanism of activation in vivo is unknown and may involve several additional enzymes. hK2 has also been shown to activate single chain urokinase-type plasminogen activator, scuPA, to the active two-chain form, uPA, which is highly correlated with prostate cancer metastasis. More recently, hK2 has been shown to inactivate the major tissue inhibitor of uPA, plasminogen activator inhibitor-1 (PAI-1). Thus hK2 may influence the progression of prostate cancer by the activation of uPA and by the inactivation of PAI-1.

Enzymatically active hK2 has also been shown to form covalent complexes in vitro with plasma protease inhibitors such as $\alpha_1$-antichymotrypsin (ACT), $\alpha_2$-antiplasmin, antithrombin III, protein C inhibitor (PCI), and $\alpha_2$-macroglobulin (AMG). hK2 has been identified in prostate cancer serum in a complex with ACT.

Thapsigargin (TG) is a sesquiterpene-γ-lactone available by extraction from the seeds and roots of the umbelliferous plant *Thapsia garganica* L. Thapsigargin selectively inhibits the sarcoplasmic reticulum (SR) and endoplasmic reticulum (ER) $Ca^{2+}$-ATPase (SERCA) pump, found in skeletal, cardiac, muscle and brain microsomes. The apparent dissociation constant for TG from the SERCA pump is 2.2 pM or less.

SUMMARY OF THE INVENTION

The present invention provides a novel class of oligopeptides that include amino acid sequences containing cleavage sites for human glandular kallikrein (HK2) (FIG. 1) (SEQ ID NOs:1-14). These cleavage sites are derived from an hK2 specific cleavage map of semenogelin I and II (FIG. 1) and from hK2 cleavable peptides isolated from a random peptide library. These oligo peptides are useful in assays that can determine the free hK2 protease activity. Furthermore, the invention also provides a therapeutic prodrug composition, comprising a therapeutic drug linked to a peptide, which is specifically cleaved by hK2. The linkage substantially inhibits the non-specific toxicity of the drug, and cleavage of the peptide releases the drug, activating it or restoring its non-specific toxicity.

The invention also provides a method for treating cell proliferative disorders, including those which involve the production of hK2, in subjects having or at risk of having such disorders. The method involves administering to the subject a therapeutically effective to amount of the composition of the invention.

The invention also provides a method of producing the prodrug composition of the invention. In another embodiment, the invention provides a method of detecting hK2 activity in tissue. In yet another embodiment, the invention provides a method of selecting appropriate prodrugs for use in treating cell proliferative disorders involving hK2-production.

The invention also provides a method for detecting a cell proliferative disorder associated with hK2 production in a tissue of a subject, comprising contacting a target cellular component suspected of having an hK2 associated disorder, with a reagent which detects enzymatically active hK2.

The invention also provides a method of determining hK2 activity in an hK2-containing sample, comprising contacting the sample with a detectably labeled peptide which is specifically cleaved by hK2 for a period of time sufficient to allow hK2 to cleave the peptide, detecting the detectable label to yield a detection level, which is then compared to the detection level obtained by contacting the same detectably labeled peptide with a standard hK2 sample of known activity.

The invention also provides a method of imaging soft tissue and/or bone metastases which produce hK2, comprising administering a lipophilic-imaging label linked to a peptide which is specifically cleaved by hK2 to a patient suspected of having an hK2-associated cell proliferative disorder, allowing hK2 to cleave the peptide, allowing the lipophilic imaging label to accumulate in the tissue and/or bone, allowing the subject to clear the uncleaved peptide, and imaging the subject for diagnostic purposes.

The invention also provides a method for identifying peptide sequences which are specifically cleaved by hK2.

Unless otherwise defined, all technical and scientific terms used herein have the ordinary meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other reference materials mentioned herein, as well as the figures and the sequence listing, are incorporated by reference in their entirety. In case of conflict, the present specification, including definitions, will control. In addition the materials, methods, and examples are illustrative only and not intended to be limiting.

BRIEF DESCRIPTION OF THE DRAWINGS

FIG. 1 depicts the amino acid sequences of peptides hydrolyzed by hK2 (SEQ ID NOs:1-14). A random peptide library was constructed with the sequence $NO_2$-Y-G-K-A-$X_1$-$X_2$-$X_3$-Dap-F-K(ABZ) (SEQ ID NO:48), wherein $NO_2$-Y is a nitrotyrosine quencher, $X_1$, $X_2$, and $X_3$ are any random L-amino acid except for cysteine (n=19), Dap is diaminopropanoate, and K(ABZ) is lysine coupled to the fluorophore aminobenzoic acid (ABZ). hK2 cleavage sites are denoted by single or double slashes (/ or //). The 14 peptide sequences shown are set forth as SEQ ID NOs:1-14, respectively. SEQ ID NOs:22-35 correspond to the peptide sequences obtained when a leucine residue is added after the $X_3$ position of SEQ ID NOs:1-14, respectively.

DETAILED DESCRIPTION OF THE INVENTION

Figure 2:
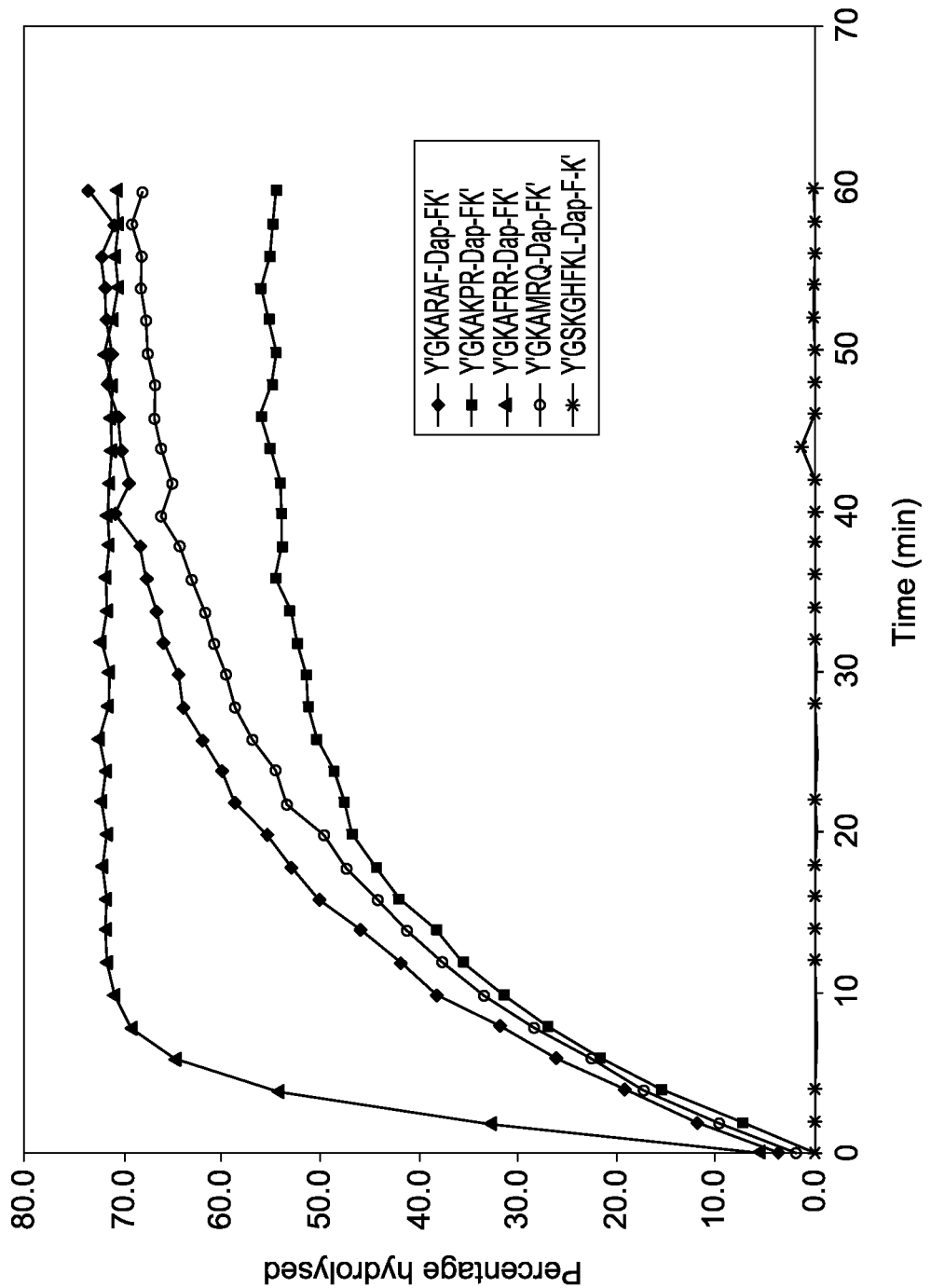
FIG. 2 depicts a graph of hK2 mediated hydrolysis of peptide substrates identified through the screening of a random peptide library. Substrates (250 µM) were incubated with 8 µg/ml hK2 in PBS buffer. Hydrolysis of peptide results in increased fluorescence, as measured using a 96 well fluorometer. Note that the double arginine substrate (Y'GKAFRR-Dap-FK') by far exceeded all other substrates. A substrate without arginine (Y'GSKGHFKL-Dap-F-K') did not show any hydrolysis. To determine 100% digestion, trypsin was added (50 mg/ml) and samples were incubated to 37° C. for 30 min and the fluorescence was determined. The percentage digested is determined by dividing fluorescence units of sample by fluorescence units of control fully digested peptide.

The invention provides a novel class of peptides that contain a cleavage site specific for human glandular kallikrein 2 (hK2). These peptides are efficiently and specifically cleaved by hK2. These peptides are useful for substantially inhibiting the non-specific toxicity of the therapeutic agents prior to the agents contracting a tissue containing hK2. Thus, the invention includes prodrugs which include peptides linked to therapeutic agents. The prodrugs of the invention comprise peptide sequences containing a cleavage site specific for hK2 and therapeutic drugs. The compositions are stable in human and mouse plasma and do not show significant non-specific toxicity, but in environments where hK2 is found, the composition becomes activated when peptide is cleaved, releasing the therapeutic drug, which regains its non-specific toxicity.

hK2 Specific Peptide

As used herein the term "human glandular kallikrein 2" (hK2) means human glandular kallikrein 2, as well as other proteases that have the same or substantially the same proteolytic cleavage specificity as hK2. As used herein, the term "naturally occurring amino acid side chain" refers to the side chains of amino acids known in the art as occurring in proteins, including those produced by post translational modifications of amino acid side to chains. The term "contacting" refers to exposing tissue to the peptides, therapeutic drugs or prodrugs of the invention so that they can effectively inhibit cellular processes, or kill cells. Contacting may be in vitro, for example by adding the peptide, drug or prodrug to a tissue culture to test for susceptibility of the tissue to the peptide, drug or prodrug. Contacting may be in vivo, for example administering the peptide, drug, or prodrug to a subject with a cell proliferative disorder, such as prostate or breast cancer. By "peptide" or "polypeptide" is meant any chain of amino acids, regardless of length or post-translational modification (e.g., glycosylation or phosphorylation). As written herein, amino acid sequences are presented according to the standard convention, namely that the amino-terminus of the peptide is on the left, and the carboxy terminus on the right. In one aspect the invention features a peptide containing an amino acid sequence that includes a cleavage site specific for hk2 or an enzyme having a proteolytic activity of hK2. The peptides of the invention are preferably not more than 20 amino acids in length, more preferably to more than ten amino acids in length, and even more preferably about 6 amino acids in length. The preferred amino acid sequences of the invention are linear. In an embodiment of the invention the amino acid sequence may be cyclical such that the cyclical form of the sequence is an inactive drug that can become an activated drug upon cleavage by hK2 and linearization.

Preferably, the peptide sequences of the invention comprise the sequence G-K-A-$X_1$-$X_2$-$X_3$, wherein at least one of $X_1$, $X_2$, and $X_3$ is an arginine residue and wherein the amino acid residues at the other two positions of $X_1$, $X_2$, and $X_3$ are any amino acid residue. hK$_2$ may cleave the peptide after either $X_1$, $X_2$, or $X_3$, and in the most preferred embodiments, hK2 cleaves the peptide after an arginine residue. Specific preferred sequences (including cleavage sites) are shown in FIG. 1. Further preferred sequences in include the sequences shown in FIG. 1, with an additional leucine residue after the $X_3$ position. In a particularly preferred embodiment, the peptides of the invention comprise the amino acid sequence of SEQ ID NO:9.

Other embodiments of peptide sequences which are useful for cleavage by hK2 and proteases with the hydrolytic activity of hK2 are disclosed in the Examples section. Further examples of the peptides of the invention are constructed as analogs of, derivatives of and conservative variations on the amino acid sequences disclosed herein. Thus, the broader group of peptides having hydrophilic and hydrophobic substitutions, and conservative variations are encompassed by the invention. Those of skill in the art can make similar substitutions to achieve peptides with greater activity and or specificity toward hK2. For example, the invention includes peptide sequences described above, as well as analogs or derivatives thereof, as long as the bioactivity of the peptide remains. Minor modifications of the primary amino acid sequence of the peptides of the invention may result in peptides that have substantially equivalent activity as compared to the specific peptides described herein. Such modifications may be deliberate, as by site directed mutagenesis or chemical synthesis, or may be spontaneous. All of the peptides produced by these modifications are included herein, as long as the biological activity of the original peptide remains, i.e. susceptibility to cleavage by hK2.

Further, deletion of one or more amino acids can also result in a modification of the structure of the resultant molecule without significantly altering its biological activity. This can lead to the development of a smaller active molecule without significantly altering its biological activity. This can lead to the development of a smaller active molecule which would also have utility. For example, amino or carboxy-terminal amino acids which may not be required for biological activity of the particular peptide can be removed. Peptides of the invention include any analog, homolog, mutant or isomer or derivative of the peptides disclosed in the present invention, as long as bioactivity described herein remains. All peptides described have sequences comprised of L-amino acids; however, D-forms of the amino acids can be synthetically produced and used in the peptides described herein.

The peptides of the invention include peptides which are conservative variations of those peptides specifically exemplified herein. The term "conservative variation" as used herein denotes the replacement of an amino acid residue by another, biologically similar residue. Examples of conserved variations include the substitution of one hydrophobic residue such as isoleucine, valine, leucine, alanine, cysteine, glycine, phenylalanine, proline, tryptophan, tyrosine, norleucine or methionine for another or the substitution of one polar residue for another such as the substitution of arginine for lysine or histidine, glutamic for aspartic acids or glutamine for asparagine, and the like. Neutral hydrophilic amino acids that can be substituted for one another include asparagine, glutamine, serine, and threonine. Such conservative substitutions are within the definitions of the classes of peptides of the invention. The peptides that are produced by such conservative variation can be screened for suitability of use in the prodrugs of the invention according to the methods for selecting prodrugs provided herein.

A wide variety of groups can be linked to the carboxy terminus of the peptides. Notably, therapeutic drugs can be linked to this position. In this way advantage is taken of the hK2 specificity of the cleavage site, as well as other functional characteristics of the peptides of the invention. Preferably, the therapeutic drugs are linked to the carboxy terminus of the peptides, either directly or through a linker group. The direct linkage is preferably through an amide bond, in order to utilize the proteolytic activity and specificity of hK2. If the connection between the therapeutic drug and the amino acid sequence is made through a linker, this connection is also preferably made through an amide bond, for the same reason. This linker may be connected to the therapeutic drug through any of the bond types and chemical groups known to those skilled in the art. The linker may remain on the therapeutic drug, or may be removed soon thereafter, either by further reactions or in a self-cleaving step. Self-cleaving linkers are those linkers which can intramolecularly cyclize and release the drug or undergo spontaneous $S_N1$ solvolysis and release the drug upon peptide cleavage.

Other materials such as detectable labels or imaging compounds can be linked to the peptide. Groups can be linked to the amino terminus of the peptides, including such moieties as antibodies, and peptide toxins, including the 26 amino acid toxin melittin and the 35 amino acid toxin cecropin B for example. Both of these peptide toxins have shown toxicity against cancer cell lines. The N-terminal amino acid of the peptide may also be attached to the C-terminal amino acid either via an amide bond formed by the N-terminal amine and the C-terminal carboxyl, or via coupling of side chains on the N-terminal and C-terminal amino acids or via disulfide bond formed when the N-terminal and C-terminal amino acids both consist of the amino acid cysteine. Further, it is envisioned that the peptides described herein can be coupled, via the carboxy terminus, to a variety of peptide toxins (for example, melittin and cecropin are examples of insect toxins), so that cleavage by hK2 liberates an active toxin. Additionally, the peptide could be coupled to a protein such that the protein is connected at the carboxy terminal amino acid of the peptide. This coupling can be used to create an inactive proenzyme so that cleavage by a tissue-specific protease (such as hK2 or PSA) would cause a conformational change in the protein to activate it. For example, Pseudomonas toxin has a leader peptide sequence which must be cleaved to activate the protein. Additionally, the peptide sequence could be used to couple a drug to an antibody. The antibody could be coupled to the N-terminus of the peptide sequence, and the drug coupled to the carboxy terminus. The antibody would bind to a cell surface protein and tissue-specific protease present in the extracellular fluid could cleave the drug from the peptide linker.

The preferred amino acid sequence can be constructed to be highly specific for cleavage by hK2. In addition the peptide sequence can be constructed to be highly selective to towards cleavage by hK2 as compared to purified extracellular and intracellular proteases. Highly-specific hK2 sequences can also be constructed that are also stable toward cleavage in human sera.

The peptides of the invention can be synthesized according to any of the recognized procedures in the art, including such commonly used methods as t-boc or fmoc protection of alpha-amino groups. Both methods involve stepwise syntheses whereby a single amino acid is added at each step starting from the C-terminus of the peptide. Peptides of the invention can also be synthesized by well-known solid phase peptide synthesis methods. Peptides can be characterized using standard techniques such as amino acid analysis, thin layer chromatography, or high performance liquid chromatography, for example.

The invention encompasses isolated nucleic acid molecules encoding the hK2-specific peptides of the invention, vectors containing these nucleic acid molecules, cells harboring recombinant DNA encoding the hK2-specific peptides of the invention, and fusion proteins that include the hK2 specific peptides of the invention. Especially preferred are nucleic acid molecules encoding the polypeptides described herein.

Prodrug Compositions

The invention also features prodrug compositions that consist of a therapeutic drug linked to a peptide containing a cleavage site that is specific for hK2 or any enzyme that has the enzymatic activity of hK2. As noted above, the peptides of the invention can be used to target therapeutic drugs for activation within hK2 producing tissue. The peptides that are useful in the prodrugs of the invention are those described above.

The therapeutic drugs that may be used in the prodrugs of the invention include any drug which can be directly or indirectly linked to the hK2-specifically cleavable peptides of the invention. Preferred drugs are those containing a primary amine. The presence of the primary amine allows for formation of an amide bond between the drug and the peptide and this bond serves as the cleavage site for hK2. The primary amines may be found in the drugs as commonly provided, or they may be added to the drugs by chemical synthesis.

Certain therapeutic drugs contain primary amines and are among the preferred agents. These include the anthracycline family of drugs, vinca drugs (e.g., vinca alkaloids such as vincristine, vinblastine, and etoposide), mitomycins, bleomycins, cytotoxic nucleoside analogs (e.g., 5-fluorouracil, gemcitabine, and 5-azacytidine), the pteridine family of drugs, diynenes, podophyllotoxins, antiandrogens (e.g., bis-calutamide, flutamide, nilutamide, and cyproterone acetate), antifolates (e.g., methotrexate), topoisomerase inhibitors (e.g., Topotecan and irinotecan), alkylating agents (e.g., cyclophosphamide, Cisplatinum, carboplatinum, and ifosfamide), taxanes (e.g., paclitaxel and docetaxel), and compounds which are useful as targeted radiation sensitizers (e.g., 5-fluorouracil, gemcitabine, topoisomerase inhibitors, and cisplatinum). Additional particulary useful members of these classes include, for example, doxorubicin, daunorubicin, caminomycin, idarubicin, epirubicin, aminopterin, methopterin, mitomycin C, porfiromycin, cytosine arabinoside, melphalan, vindesine, 6-mercaptopurine, and the like, including any therapeutic drug (e.g., any therapeutic drug used in the treatment of cancer, including prostate and/or breast cancer) known to those of skill in art.

Other therapeutic drugs are required to have primary amines introduced by chemical or biochemical synthesis, for example sesquiterpene-lactones such as thapsigargin, and thapsigargicin and many others know to those skilled in the art. The thapsigargins are a group of natural products isolated from species of the umbelliferous genus *Thapsia*. The term thapsigargins has been defined by Christensen, et al., *Prog. Chem. Nat. Prod.*, 71 (1997) 130-165. These derivatives contain a means of linking the therapeutic drug to carrier moieties, including peptides and antibodies. The peptides and antibodies can include those which specifically interact with antigens including hK2. The interactions can involve cleavage of the peptide to release the therapeutic analogs of sesquiterpene-γ-lactones. Particular therapeutic analogs of sesquiterpene-γ-lactones, such as thapsigargins, are disclosed in U.S. Pat. Nos. 6,265,540 and 6,410,514, both of which are incorporated herein in their entireties.

For example, thapsigargins with alkanoyl, alkenoyl, and arenoyl groups at carbon 8 or carbon 2, can be employed in the practice of the invention disclosed herein. Groups such as $CO-(CH=CH)_{n1}-(CH_2)_{n2}-Ar-NH_2$, $CO-(CH_2)_{n2}-(CH=CH)_{n1}-Ar-NH_2$, $CO-(CH_2)_{n2}-(CH=CH)_{n1}-CO-NH-Ar-NH_2$ and $CO-(CH=CH)_{n1}-(CH_2)_{n2}-CO-NH-Ar-NH_2$ and substituted variations thereof can be used as carbon 8 substituents, where n1 and n2 are from 0 to 5, and Ar is any substituted or unsubstituted aryl group. Substituents which may be present on Ar include short and medium chain alkyl, alkanoxy, aryl, aryloxy, and alkenoxy groups, nitro, halo, and primary secondary or tertiary amino groups, as well as such groups connected to Ar by ester or amide linkages.

In other embodiments of thapsigargin analogs, these substituent groups are represented by unsubstituted, or alkyl-, aryl-, halo-, alkoxy-, alkenyl-, amino-, or amino-substituted $CO-(CH_2)_{n3}-NH_2$, where n3 is from 0 to 15, preferably 3-15, and also preferably 6-12. Particularly preferred substituent groups within this class are 6-aminohexanoyl, 7-aminoheptanoyl, 8-aminooctanoyl, 9-aminononanoyl, 10-aminodecanoyl, 11-aminoundecanoyl, and 12-aminododecanoyl. These substituents are generally synthesized from the corresponding amino acids, 6-aminohexanoic acid, and so forth. The amino acids are N-terminal protected by standard methods, for example Boc protection. Dicyclohexylcarbodiimide (DCCl)-promoted coupling of the N-terminal protected substituent to thapsigargin, followed by standard deprotection reactions produces primary amine-containing thapsigargin analogs.

The substituents can also carry primary amines in the form of an amino amide group attached to the alkanoyl-, alkenoyl-, or arenoyl substituents. For example, C-terminal protection of a first amino acid such as 6-aminohexanoic acid and the like, by standard C-terminal protection techniques such as methyl ester formation by treatment with methanol and thionyl chloride, can be followed by coupling the N-terminal of the first amino acid with an N-protected second amino acid of any type.

In a preferred embodiment, the thapsigargin analog or derivative is 8-O-(12-[L-leucinoylamino]dodecanoyl)-8-O-debutanoylthapsigargin, also referred to herein as "L12ADT".

The peptide and therapeutic drug are linked directly or indirectly (by a linker) through the carboxy terminus of the peptide. The site of attachment on the therapeutic drug must be such that, when coupled to the peptide, the non-specific toxicity of the drug is substantially inhibited. Thus the prodrugs should not be significantly toxic.

The peptides and prodrugs of the invention may also comprise groups which provide solubility to the peptide or prodrug as a whole in the solvent in which the peptide or prodrug is to be used. Most often the solvent is water. This feature of the invention is important in the event that neither the peptide nor the therapeutic drug is soluble enough to provide overall solubility to the peptide or prodrug. These groups include polysaccharides or other polyhydroxylated moieties. For example, dextran, cyclodextrin, starch and derivatives of such groups may be included in the peptide or prodrug of the invention. In a preferred embodiment, the group which provides solubility to the peptide or prodrug is a polymer, e.g., polylysine or polyethylene glycol (PEG).

Thapsigargin Analogs

The invention also features derivatized thapsigargin analogs with the derivatization including providing the molecule with a residue substituted with a primary amine. The primary amine can be used to link the derivatized thapsigargin analog with various other moieties. Among these are peptides which link to the analog to give prodrugs without significant non-specific toxicity, but enzymatic reaction with hK2 affords the toxic drug. These enzymatic reactions can liberate the non-specific toxic thapsigargin derivative, for example by cleavage through proteolysis or hydrolysis, various reactions of the side chains of the peptide, or other reactions which restore the non-specific toxicity of the thapsigargin analog. These reactions can serve to activate the derivatized thapsigargin analog locally at hK2 producing tissue, and with relative exclusivity to regions in which these enzymatic reactions take place. The primary amine containing thapsigargin analog can also be linked to an antibody, oligonucleotide, or polypeptide which binds to an epitope or receptor in the target tissue.

Thapsigargin is a sesquiterpene-γ-lactone having the following structure. Primary amines can be placed in substituent groups pendant from either C-2 or C-8 carbon. Preferred primary amine containing thapsigargin analogs that can be coupled to the peptides described above include those described in U.S. Pat. Nos. 6,265,540 and 6,410,514. These primary amine-containing analogs have non-specific toxicity toward cells. This toxicity is measured as the toxicity needed to kill 50% of clonogenic cells ($LC_{50}$). The LC50 of the analogs of this invention is desirably at most 10 μM, preferably at most 2 μM and more preferably at most 200 nM of analog.

Methods of Treatment Using Prodrugs

The invention also provides methods of treatment of treating hK2-producing cell proliferative disorders of the invention with the prodrugs of the invention. The prodrugs of the invention and/or analogs or derivatives thereof can be administered to any host, including a human or non-human animal, in an amount effective to treat a disorder.

The prodrugs of the invention can be administered parenterally by injection or by gradual infusion over time. The prodrugs can be administered intravenously, intraperitoneally, intramuscularly, subcutaneously, intracavity, or transdermally. Preferred methods for delivery of the prodrug include intravenous or subcutaneous administration. Other methods of administration, as well as dosing regimens, will be known to those skilled in the art.

Method of Producing Prodrugs

The invention provides a method of producing the prodrugs of the invention. This method involves linking a therapeutically active drug to a peptide of the invention described above. In certain embodiments the peptide is linked directly to the drug; in other embodiments the peptide is indirectly linked to the drug via a linker. In each case the carboxy terminus of the peptide is used for linking. That is, in an amino acid sequence G-K-A-$X_1$-$X_2$-$X_3$ (SEQ ID NO:17), the link is established through $X_3$. The therapeutic drug contains a primary amine to facilitate the formation of an amide bond with the peptide. Many acceptable methods for coupling carboxyl and amino groups to form amide bonds are know to those skilled in the art.

The peptide may be coupled to the therapeutic drug via a linker. Suitable linkers include any chemical group which contains a primary amine and include amino acids, primary amine-containing alkyl, alkenyl or arenyl groups. The connection between the linker and the therapeutic drug may be of any type know in the art, preferably covalent bonding.

In certain embodiments, the linker comprises an amino acid or amino acid sequence. The sequence may be of any length, but is preferably between 1 and 10 amino acids, most preferably between 1 and 5 amino acids. Preferred amino acids are leucine or an amino acid sequence containing this amino acid, especially at their amino termini.

Method of Screening Tissue and Determining hK2 Activity

In another aspect the invention provides a method of detecting hK2-producing tissue using peptides of the invention, as described above. The method is carried out by contacting a detectably labeled peptide of the invention with target tissue for a period of time sufficient to allow hK2 to cleave the peptide and release the detectable label. The detectable label is then detected. The level of detection is compared to that of a control sample not contacted with the target tissue. Many varieties of detectable labels are available, including optically based labels such as chromophoric, chemiluminescent, fluoresecent or phosphorescent labels and radioactive labels, such as alpha, beta, or gamma emitting labels. In addition a peptide label consisting of an amino acid sequence can be utilized for detection such that release of the peptide label by hK2 proteolysis can be detected by high pressure liquid chromatography. The peptide sequences of the invention can also be incorporated into the protein sequence of a fluorescent protein such that cleavage of the incorporated hK2 specific sequence by hK2 results in either an increased or decreased fluorescent signal that can be measured using the appropriate fluorometric measuring instrument. In a preferred embodiment, the peptide comprises a fluorescent label at its carboxy terminus (e.g., L(ABZ)), and a quencher at its amino terminus (e.g., a nitrotyrosine residue), such that the label is quenched when the to peptide is intact, and fluorescent when the peptide is cleaved.

The invention provides a method for detecting a cell proliferative disorder that comprises contacting an hK2-specific peptide with a cell suspected of producing hK2. The hK2 reactive peptide is labeled by a compound so that cleavage by hK2 can be detected. For purposes of the invention, a peptide specific for hK2 may be used to detect the level of enzymatically active hK2 in biological tissues such as saliva, blood, urine, and tissue culture media. In an embodiment of the method a specific hK2 inhibitor is used to confirm that the activity being measured is solely due to peptide cleavage by hK2 and not secondary to non-specific cleavage by other proteases present in the biological tissue being assayed. Examples of hK2 inhibitors that can be employed in the method include the addition of zinc ions, or the addition of hK2 specific antibodies that bind to the catalytic site of hK2 thereby inhibiting enzymatic activity of hK2.

Method of Screening Prodrugs

The invention also provides a method of selecting potential prodrugs for use in the invention. The method generally consists of contacting prodrugs of the invention with hK2-producing tissue and non-hK2 producing tissue in a parallel experiment. The prodrugs which exert toxic effects in the presence of hK2-producing tissue, but not in the presence of non-hK2 producing tissue are suitable for the uses of the invention.

Method of Identifying Peptide Sequences Which are Substrates for hK2

The invention also provides a method for identifying peptide sequences which are substrates for hK2. The method generally comprises generating a library of random peptides, incubating the peptides with hK2, detecting the peptides which are cleaved by hK2, and determining the sequence of the cleaved peptides. In a preferred embodiment, the peptides comprise a label which is undetectable when the peptides are intact, but detectable when they are cleaved. In a further preferred embodiment, the peptides are attached to a mechanical support (e.g., a bead), and the cleaved peptides can be separated manually from the intact peptides. More specific details for performing the method may be found in the Examples below.

This invention is further illustrated by the following examples which should not be construed as limiting. The contents of all references, patents, and published patent applications cited throughout this application, as well as the figures and the sequence listing, are incorporated herein by reference.

EXAMPLES

Materials and Methods

The following materials and methods were used in Examples 1-5 unless otherwise specified.

Materials

A mutant form of hK2 was utilized in which the amino acids −5 to −1 of the propeptide sequence of hK2 (i.e.Leu-Ile-Gln-Ser-Arg; SEQ ID NO:15) were mutated to Asp-Asp-Asp-Asp-Lys (SEQ ID NO:16) to generate a pro-hK2 protein that can be activated to functional hK2 by factor Xa (Lovgren, J. et al. (1999) Eur. J. Biochem. 266:1050-1055). Compared with wild-type hK2, expression of the propeptide hK2 mutant increases the expression levels up to 15-40-fold (Lovgren, J. et al. (1999) Eur. J. Biochem. 266:1050-1055). The generation and characteristics of this mutant hK2 have been previously described (Lovgren, J. et al. (1999) Eur. J. Biochem. 266:1050-1055).

Fmoc amino acids were purchased either from Advanced Chemtech (Louisville, Ky. or Novabiochem (San Diego, Calif.). Reagents were used without further purification. All other reagents were from Sigma Chemical Co. (St. Louis, Mo.) unless otherwise specified in the text.

Immobilized Peptide Synthesis and Hydrolysis Determination

Peptides ("PepSpots") were provided by Jerini Biotools (Berlin, Germany) and were synthesized on continuous cellulose assays using the SPOT-synthesis technique (Kramer, A. et al. (1999) J. Pept. Res. 54:319-327). Each peptide contained an amino-benzoic acid (Abz) moiety at the N-terminus. Abz is a fluorescent molecule with optimal excitation at 325 nm and emission maxima at 420 nm. Peptides were synthesized on cellulose membranes then punched out as small disks into 96-well microtiter plates. Approximately 8 nmoles of peptide are synthesized per spot.

To perform protease assay, spots were rinsed first for 5 minutes with 200 ml of methanol in order to solubilize peptides. Spots were then rinsed 4 times for 10 minutes under gentle agitation with a buffer consisting of 50 mM Tris and 0.1 M NaCl, pH 7.8 (Buffer A). Fresh buffer A was added to each well along with an aliquot of purified protease (i.e. mutant hK2 or trypsin) or 50% human serum in was buffer A. The plate was sealed with plastic and reaction allowed to occur at room temperature without agitation. At described intervals (i.e. 1, 2, 4, 7 and 24 hrs) a 50 ml aliquot of the reaction mixture was transferred to a new 96-well microtiter plate. Fluorescence was then measured at room temperature using a 96-well fluorometric plate reader (Fluoroscan II) with excitation of 355 nm and emission 408 nm. Fluorescence at each point was plotted and reaction rates determined from slope of the best-fit line. Rates are expressed in relative fluorescence units/hr/mg of protease.

Combinatorial Libraries

Combinatorial peptides libraries were synthesized as described in (St. Hilaire, P. M. et al. (1999) J. Comb. Chem. 1:509-523). Peptides were anchored to the resin without a cleavable linker. Initially, TentaGel resin (Advanced Chemtech, Louisville Ky., 0.3 mmoles/g, 130 microns) was chosen as a solid support but this resin seemed incompatible with on-resin proteolysis. The PEGA support (Polymerlabs, Amherst Mass., 400 microns, 0.2 mmoles/g) proved more successful.

Amino acid couplings were performed according to established Fmoc/tBu protocols using Hobt/DIC activation (Chan, W. and White, P. Fmoc solid phase peptide synthesis, a practical approach. New York: Oxford University, 2000) and performing standard double couplings. Generally, completion of acylation reactions was verified by both Ninhydrin (Kaiser, E. et al. (1970) Anal. Biochem. 34:595-598) and fluorescamine testing (Felix, A. M. and Jimenez, M. H. (1973) Anal. Biochem. 52:377-381). Deprotection of the side-chain protecting group was performed by using Reagent K (TFA/thioanisole/water/phenol/EDT 82.5:5:5:5:2.5 v/v). The Fmoc protecting group was removed with 25% piperidine in DMF. N-α-Fmoc-N-β-t-Boc-L-diaminopropionic acid (Fmoc-Dpr(Boc)-OH, Novabiochem) was used for the introduction of Dap. Three randomized positions were introduced using a Labmate parallel Organic Synthesizer (4×6 vessels, Advanced Chemtech, Louisville, Ky.) according to the split-and-mix procedure (Houghten, R. A. (1985) Proc. Natl. Acad. Sci. USA 82:5131-5135). All natural amino acids, except for cysteine were used with the following side-chain protection: Trt (Asn, Gln, His), tBu (Tyr), OtBu (Asp, Glu, Ser, and Thr), Boc (Lys, Trp) and Pmc (Arg). Amino acid stock solutions (0.5 M with 0.5 M Hobt) were mixed with DIC for 20 min (4 Eq. of each). The activated amino acids were added to the resin and 0.15 ml of 5% DIEA in DMF was added. After 2-3 hrs, the resin aliquots were washed (3×NMP, 3×MeOH, 3×DMF) and couplings were repeated with 2 eq. amino acid for 1-2 hrs. A resin sample of each aliquot was subjected to a Ninhydrin and a fluorescamine test which showed completion of the acylation reactions in all cases. Next, the resin aliquots were pooled [FmocX$_1$-X$_2$-X$_3$-Dap-Phe-K(Abz)-PEGA] (SEQ ID NO:50) was deprotected with piperidine and the remaining four constant residues, alanine, lysine, glycine and nitrotyrosine (Y', Fluka) were added as Fmoc amino acids in batch with Hobt/DIC activation as described above. For the final deprotection of the side chains, the resin was suspended in Reagent K (1 ×10 min, 1×3 hrs). The resin was washed with 95% acetic acid (3×), DCM (3×), DMF (3×), 5% DIEA in DMF (3×), and DMF (6×). The resin was stored until screening suspended in DMF at −20° C.

For screening, approximately 1 ml of resin (~65,000 beads) was first suspended in methanol in a Petri dish and examined under transilluminant UV light (302 nm) to detect any falsely positive fluorescent beads prior to addition of protease. After removal of ~40-50 beads, the resin was washed with water and finally suspended in 10 ml buffer in a glass Petri dish. After a final screen for false-positives, hK2 was added from a frozen stock solution to make 4 µg/ml final. Fluorescent beads were selected and removed with a micropipette, washed with 1 M NaCl, water, DMF, MeOH, water and stored in MeOH at −20° C.

Peptide Sequencing

Peptide sequencing was completed using an Applied Biosystem 477A Protein/Peptide sequencer (Edman chemistry) interfaced with a 120A HPLC(C-18 PTH column, reverse-phase chromatography) analyzer to determine phenylthiohydantoin (PTH) amino acids.

Automated Synthesis of Fluorescence-quenched Peptides

For validation of the Edman results, peptides were re-synthesized using a Rainin PS3 peptide synthesizer with HBTU/NMM activation. Peptides were synthesized on PEGA resin for on-bead analysis or on Fmoc-Lys(Mtt)-Wang resin for solution assays. The Fmoc-Lys(Mtt)-Wang resin was first deprotected with 2% TFA in DCM (3×2 min). The ε-amine of lysine was then acylated with Boc-Abz. Deprotection/cleavage was performed in TFAJTIS/water (95:2.5: 2.5 v/v) for 2-3 hours. Peptides were ether precipitated, dried and purified by C18-HPLC using a linear gradient of acetonitrile (0.1% TFA), lyophilized and dissolved in DMSO. Peptide identities were confirmed by analysis on a Perseptive Voyager DE-STR MALDI-TOF using dihydroxy benzoic acid as a matrix. Fluorescence measurements were performed on a Fluoroskan II 96-well plate reader (ICN biomedicals, Costa Mesa, Calif.; excitation, 355 nm; emission, 460 nm). Kinetic parameters were calculated as described earlier (Denmeade, S. R. et al. (1997) Cancer Res. 57:4924-4930).

Plasma Stability Assays

Mouse plasma was obtained from cardiac puncture of anesthetized mice prior to euthanization by $CO_2$ overdose according to protocols approved by the Johns Hopkins Animal Care and Use Committee. Human plasma was obtained from discarded, pooled, and unlabeled clinical samples. Plasma was diluted to 50% in Tris buffer (50 mM Tris-HCl, 100 mM NaCl, pH 7.8). To this, test peptides/prodrugs were added to 250 or 500 µM final concentration. After the incubation period, one volume (200 µl) of acetonitrile was added to precipitate the protein fraction and the tube was centrifuged at 14,000 for 2 min. The supernatant was analyzed by C18-HPLC and the collected peaks were analyzed by MALDI-TOF as described above.

Peptide-prodrug Synthesis

The peptide sequence GKAFRRL (SEQ ID NO:18) was synthesized on a Rainin PS3 automated peptide synthesizer on Fmoc-Leu-Wang resin (100 µmoles scale). The same protecting groups were used as during the combinatorial synthesis, except for the lysine, which was orthogonally protected with the ivDde group (Fmoc-Lys(ivDde)-OH, Novobiochem). After deprotection of the N-terminal glycine, the amine was acetylated with acetic anhydride and NMM.

Deprotection of the acid-labile protecting groups and purification was performed as outlined above. Boc-12 ADT was synthesized as previously described (Jakobsen, C. M. et al. (2001) J. Med. Chem. 44:4696-4703). TFA treatment, followed by semi-prep HPLC and lyophilisation afforded the amine containing 12ADT. The protected peptide [ac-GK(ivDde)AFRRL] (SEO ID NO:51) was coupled to 12ADT after Hobt/DIC activation. After completion of the reaction, the ivDde group was removed by adding hydrazine to the reaction mixture (2% final, 30 min). Semi-preparative HPLC yielded acGKAFRRL-12ADT (SEQ ID NO:41), typically in 60-70% yield. Product was confirmed by MALDI-TOF analysis.

Determination of Plasma Levels of ac-GKAFRR-L12ADT (SEQ ID NO:41)

Calibration standards consisted of ac-GKAFRR-L12ADT prodrug, RL12ADT or L12ADT spiked into mouse plasma and plasma samples from treated mice were analyzed by liquid chromatography coupled to a quadrupolequadripole mass spectrometer (LC/MS/MS) [PESciex API 3000]. A multistep gradient elution HPLC method was used to separate the ac-GKAFRR-L12ADT prodrug from the free RL12ADT and L12ADT with eluent A=2 mM ammonium acetate with 0.1% formic acidl % acetic acid in deionized water and eluent B=90% acetonitrile/1% acetic acid/0% deionized water. Samples were eluted through a Zorbax SB-C18 Rapid Resolution column (2/1×30 mm, 3.5 µm) at a flow rate of 0.3 ml/min and gradient of 100% A to 100% B over 12 minutes. Calibration was done using extracted standards of ac-GKAFRR-L12ADT added to and then extracted from mouse plasma in a range of 0.001-10 µM, and linear regression analysis was used to generate best-fit lines, from which peak areas of samples were converted to concentration of prodrug. Peak areas of RL12ADT and L12ADT were below limit of detection at all time points and, therefore, calibration was not performed. Single-dose pharmacokinetics were assessed by noncompartmental analysis (Gibaldi, M. and Perroer, D. *Pharmacokinetics,* 2nd edition, p. 407-409. New York, 1982) The area under the curve from time zero to infinity (AUC0-∞) was calculated with the linear trapezoidal method (Gibaldi, M. and Perroer, D. Pharmacokinetics, 2nd edition, p. 407-409. New York, 1982)). The terminal half-life (T1/2) was determined from the terminal slope (ke) on a log-linear plot of concentration versus time.

In vivo Toxicity Assays

To determine in vivo toxicity of ac-GKAFRR-L12ADT, Balb-C mice (Harlan) received a single intravenous injection of an increasing dose of prodrug. Mice were monitored for toxicity hourly for twelve hours and then daily x one week. Separate groups of three mice each received increasing doses of ac-GKAFRRL12ADT. Dose escalation was stopped at the dose level that resulted in death of all mice after 24 hours (i.e. $LD_{100}$). All animals receiving doses less than $LD_{100}$ were alive and well up to 1 week after receiving a single dose. All procedures were performed according to protocols approved by the Johns Hopkins Animal Care and Use Committee Example 1

Identification of Peptide Sequences which are Substrates for hK2 Through Screening of a Combinatorial Library Trypsin and trypsin-like proteases have a defined preference for the amino acid arginine or lysine at the site of hydrolysis. There are a large number of trypsin-like proteases present in human blood, including human kallikrein 1, plasmin, thrombin, and other members of the clotting factor cascade. The proteolytic activity of these proteases in the blood is tightly regulated and these proteases are present in the bloodstream predominantly as inactive zymogens. $HK_2$ is also a trypsin-like protease with a preference or, perhaps, a requirement, for arginine at the P1 hydrolysis site (Mikolajczyk, S. D. et al: (1998) Prostate 34:44-50). However, previous data indicates that peptide substrates containing arginine are relatively unstable in the blood. Therefore, in an attempt to identify a more selective hK2 substrate that, perhaps, would not contain arginine, a larger number of peptide substrates were screend. To accomplish this screening and further investigate the sequence requirements for hK2 hydrolysis, synthesized a large fluorescent-quenched combinatorial peptide library was synthesized.

Previously, Meldal and co-workers demonstrated that protease substrate requirements can be routinely mapped by on-bead (i.e. resin) digestion of short peptides (St. Hilaire, P. M. et al. (1999) J. Comb. Chem. 1:509-523). By following the 'split- and mix' approach (Houghten, R. A. (1985) Proc. Natl. Acad. Sci. USA 82:5131-5135) a peptide library is generated on polymeric solid-phase synthesis resin "beads" so that each bead contains at the end a unique but random peptide sequence. These peptides are bracketed by a fluorophore at the C-terminus [2-amino benzoic acid (Abz) coupled to the $\epsilon$-amino group of lysine] and a pairing quencher moiety at the N-terminus (3-nitro tyrosine). Upon hydrolysis of any backbone amide bond, the quencher-containing N-terminal part of the peptide is liberated and diffuses into the solution, resulting in bright fluorescence due to un-quenching of the remaining C-terminal part, still linked to the bead (St. Hilaire, P. M. et al. (1999) J. Comb. Chem. 1:509-523). The polymeric support has to swell sufficiently in water to allow diffusion of the protease into the bead. Two types of resins that comply with this requirement are TentaGel (a mix of polystyrene and polyethylene glycol) and PEGA (a mix of polyacrylamide and polyethylene glycol). Since the former bead has greater mechanical stability, we initially synthesized a peptide library on TentaGel resin. Previous data, using the SPOT-based peptides, suggested that the positively charged tripeptide GKA would be a close-to-optimal P6-P4 amino acid sequence and that the C-terminal positions were of more significance for defining selectivity of hK2 activity. Therefore, this library was biased in that, between the N-terminal lysine-ABZ fluorophore and the C-terminal nitrotyrosine quencher a constant tripeptide (GKA) was inserted in positions P6-4 followed by random amino acids in positions P3-P1 (i.e. GKAXXX; SEQ ID NO:17).

Using this strategy, an initial redundant peptide library was synthesized according to the 'split-and-mix' procedure using TentaGel solid phase resin. All natural amino acids, excluding cysteine were used, generating a library of $19^3$=6859 members. Approximately 40,000 beads were assayed so that each peptide sequence was present several times. After careful removal of false-positive beads, the library was incubated with hK2 and several positive beads were selected over a 20-hour period. Edman sequencing of these beads revealed exclusively erratic results, describing peptides of 3 to 9 residues in length with no clear hydrolysis pattern emerging. Re-synthesis of some of these peptide sequences confirmed that these sequences were not hK2 substrates. To test the validity of this TentaGel library, a large number of beads (15-20,000) were incubated, suspended in PBS buffer, with 100 μg/ml of trypsin. Under these conditions, a large number of beads should become fluorescent due to trypsin digestion. However, after several hours at 37° C., only a very few fluorescent beads were generated. From these results it was concluded that the fluorescence-quenched libraries of this type should not be screened on the TentaGel resin. Possible explanations for this lack of significant hydrolysis of any peptide might involve the unfavorable display of the bead-linked peptide substrates or poor penetration of these proteases into the TentaGel bead.

These studies suggested that alternative resin supports and/or linkers would be required to generate libraries for screening purposes. Synthesis of a test hK2 peptide substrate on polyethylene glycol A (PEGA) resin [Y'GKAFRLK'-PEGA, (SEQ ID NO:52) where Y' is 3-nitrotyrosine and K' is Lysine (Abz)] demonstrated the importance of the resin support since this peptide was digested to yield fluorescent beads after 10-12 hours of incubation with 4 μg/ml hK2.

Figure 6:
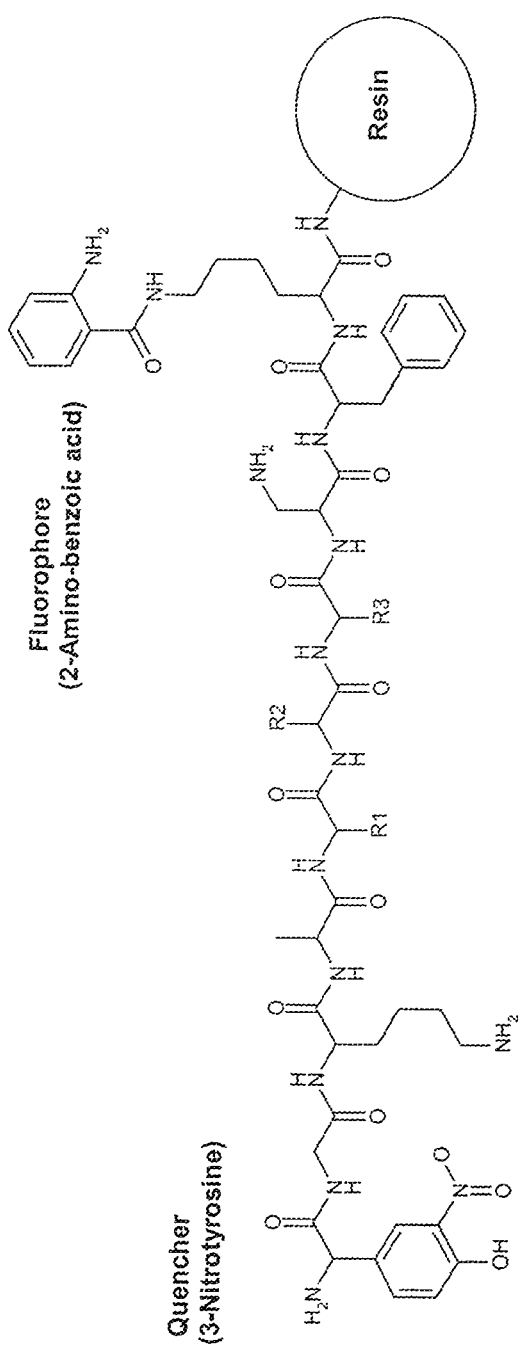
FIG. 6 depicts the chemical structure of fluorescence-quenched combinatorial 'one bead-one peptide' library [Y'GKAXXX-Dap-F-K'-PEGA, (SEQ ID NO:49) where Y' is nitrotyrosine and K' is 2-aminobenzoic acid substituted lysine].

Additionally, Walle and co-workers (Thorpe, D. S. and Walle, S. (2000) Biochem. Biophys. Res. Commun. 269:591-595) published data from a small combinatorial library to find linkers for the optimal display of peptide ligands to various protein targets. They reported that the insertion of a dipeptide consisting of a cationic residue together with a hydrophobic residue presents a general method for optimizing peptide display on solid phase beads. To test this observation in the system used herein, a linker described by Walle et al., in which the cationic residue was diamino propanoic acid (Dap) and the hydrophobic residue was phenylalanine (F), was incorporated. The test peptide Y'GKAFRL-Dap-F-K'-PEGA (SEQ ID NO:53) was synthesized and observed that the time required to generate clearly detectable fluorescence on the beads was reduced to 4-5 hours compared to 10-12 hours for the same peptide sequence lacking the Dap-F linker. On the basis of these results, the Dap-F dipeptide linker was included in all subsequent libraries. The final structure of the library is shown in FIG. 6.

Screening the Peptide Library to Identify hK2 Substrates

The final library used for screening with hK2 contained the general sequence Y'GKAX$_1$X$_2$X$_3$-Dap-F-K' PEGA (SEQ ID NO:49) where X=any of 19 amino acids (cysteine was excluded from library) and contained 193 sequences on ~50,000 beads (i.e. ~7 beads for each unique peptide sequence). After carefully removing any false positive fluorescent beads from the library (~40-50 beads), purified, enzymatically active hK2 was added at a final concentration of 4 μg/ml. After 1 hour, the first positive bead was removed. Over the subsequent 3 hours, 9 more beads were selected. In total, 14 beads were selected over a period of 24 hours. Positive beads were sequenced by Edman degradation. The sequences of the fourteen peptides are shown in FIG. 1.

Seven out of fourteen peptides contained one or more arginine residues. The peptides lacking any arginine did not show a specific amino acid preference. In order to confirm that the selected sequences represented true hK2 substrates and not false positives, the majority of the peptides were re-synthesized, cleaved from the resin and tested for hydrolysis by hK2 in solution. After re-synthesis, the soluble non-arginine containing peptides were not hydrolyzed by hK2, confirming the suspicion that the arginine-free sequences were not hK2 substrates but false positives probably generated by a combination of events. An additional attempt to identify arginine-free hK2 substrates was made by replacing arginine with lysine in the P1 position of known hK2 substrates. The P1-arginine in the SgI/II sequence GSKGHFRL (SEQ ID NO:19) was substituted for lysine and tested in solution as a fluorescence-quenched peptide as well as derivatives of this sequence (Y' GSKGHFKL-Dap-K' and Y'GSKGPFKL-Dap-K'). The arginine-free sequence GSKGHFHL (SEQ ID NO:20), identified as a substrate in the SPOT analysis was also synthesized for testing in solution (Y'GSKGHFHL-Dap-K'). Once again, none of these three arginine free peptides were digested by hK2, even after prolonged incubation. These results further support results from earlier studies using small peptide substrates and phage display and reaffirm that hK2 has a strict requirement for arginine in the P1 position of peptide substrates.

The combinatorial screen identified seven arginine-containing peptides. Four of these were re-synthesized ($X_1$-$X_2$-$X_3$=RAF, KPR, FRR and MRQ respectively). Three other lead sequences were not re-synthesized ($X_1$-$X_2$-$X_3$=IQR, FRK and VRQ respectively). All four arginine-containing sequences that were re-synthesized reproduced fluorescence when these peptides were digested on-bead with hK2. For a more quantitative analysis, the fluorescence-quenched peptides were cleaved off the resin and purified by HPLC. The rate of hydrolysis was quantified by measuring increase in fluorescence (Figure). The best substrate proved to be the sequence with arginine at P1 and P2 (i.e. Y'GKAFRR-Dap-F-K'). In less than five minutes, more than 50% of the peptide was digested (500 µM peptide, 4 µg/ml hK2). For the other peptides, digestion of the same amount of peptide took 19-29 minutes. Maximum digestion never exceeded more than 70-75%, a value that was reached with Y'GKAFRR-Dap-F-K' in less than 15 minutes. In subsequent studies, hydrolysis rates using the Y'GKAFRR-Dap-F-K' peptide were analyzed by Lineweaver-Burke reciprocal plots. The Michaelis-Menten constant ($K_m$) was determined at 26.5 µM, the $k_{cat}$ 1.09 sec$^{-1}$ and the $k_{cat}/K_m$ ratio was 41,132 sec$^{-1}$ M$^{-1}$. These results compare favorable to those previously reported for the Pro-Phe-Arg-AMC substrate used to assay hK2 activity ($K_m$ 40 µM; $k_{cat}$ 0.92 sec$^{-1}$; $k_{cat}/K_m$ 22,916 sec$^{-1}$ M$^{-1}$) and were superior to the GKAFR-AMC substrate we generated based on results of SPOT analysis ($K_m$ 146 µM; $k_{cat}$ 0.13 sec$^{-1}$; $k_{cat}/K_m$ 895 sec$^{-1}$ M$^{-1}$).

Example 2

Stability of hK2 Peptides in Plasma

Figure 7:
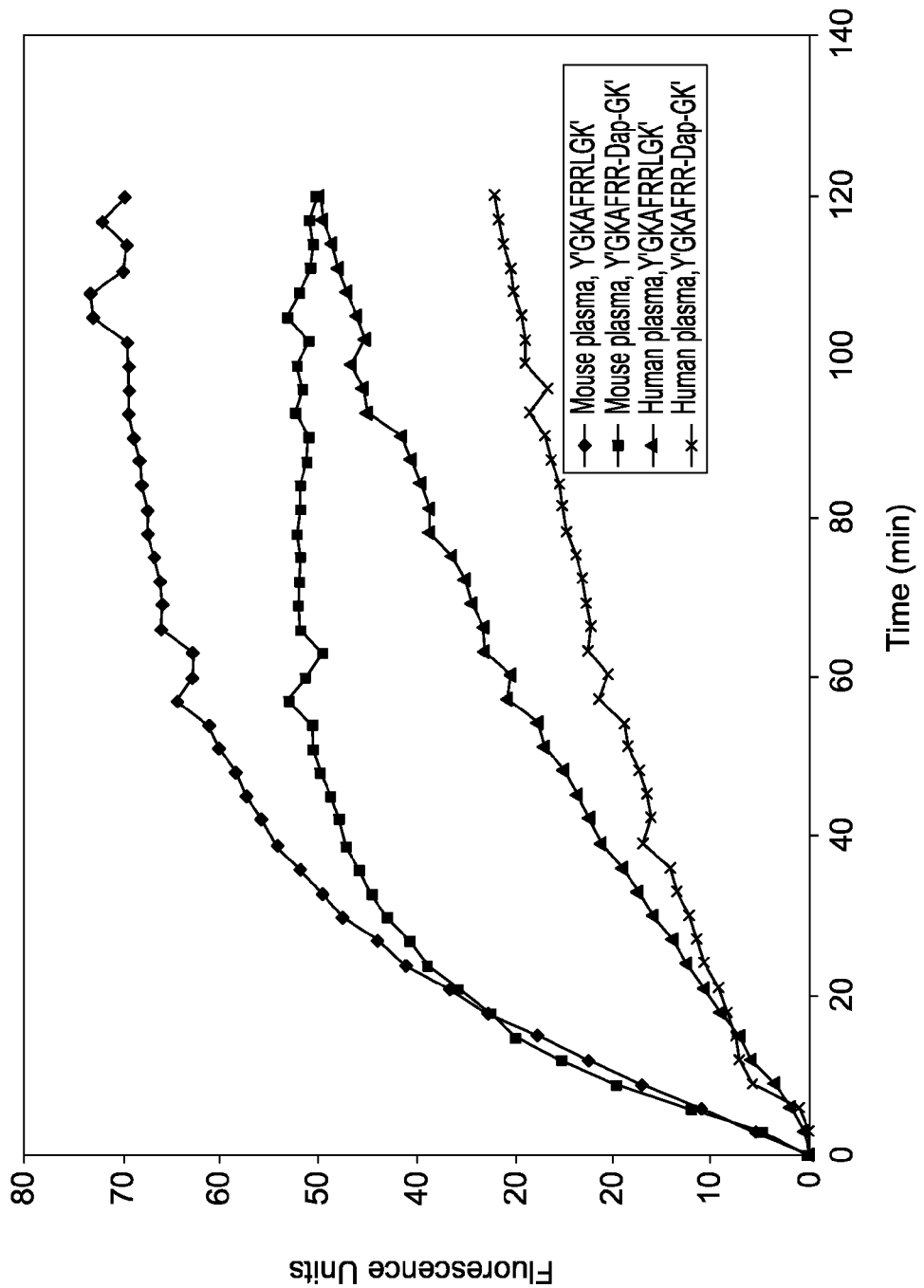
FIG. 7 depicts hydrolysis of hK2 peptide substrates [Y'GKAFRRLGK' (SEQ ID NO:21) and Y'GKAFRR-Dap-GK' (SEQ ID NO:42)] in plasma. Arginine containing lead hK2 substrates (500 mM) were incubated in 50% mouse or human plasma. Generation of fluorescence indicated that the fluorescence-quenched peptides are unstable in plasma. Hydrolysis of the substrates was confirmed by HPLC. Comparison of mouse and human plasma for the same substrate suggest higher proteolytic activity in mouse plasma compared to human plasma.

Arginine-containing peptides are potential substrates for the wide variety of other trypsin-like proteases that are present in the blood and may have residual activity in the blood. The plasma stability of an hK2 peptide substrate may therefore be limited and this would have significant consequences related to the development of an hK2 activated prodrug. Therefore, two fluorescence quenched hK2 peptide substrates peptides were incubated in 50% mouse or human plasma (diluted in PBS buffer) to determine stability using a plate-reader. As observed with arginine containing peptides from the SPOT analysis above, none of the arginine-containing, fluorescence quenched hK2 peptide substrates were stable in human or mouse plasma. Fluorescence-quenched Y'GKAFRR-Dap-GK' and Y'GKAFRRLGK' (500 µM each) were hydrolyzed when incubated in 50% mouse or human plasma (FIG. 7). Mouse plasma degraded the peptides faster than human plasma (FIG. 7). The Leucine containing peptide was less stable than the Dap containing peptide in both plasma types. HPLC analysis of the peptides after 3 hours of incubation confirmed that the fluorescence generated during this plate reader assay corresponded with proteolysis; almost no parent peptide remained after 3 hours in mouse plasma (~5%). In human plasma, more peptide remained after 3 hours (~25%). Several degradation products were generated, probably caused by the action of several exo- and endoproteolytic activities. Overnight incubation in human plasma resulted in complete degradation of both peptides. The proteolytic activity from plasma was never affected by repeated freeze-thaw cycles or by storage of the mouse plasma alone at room temperature for several days.

Example 3

Preparation and Analysis of Peptide-Coupled Prodrugs

The preceding results would suggest that the development of an hK2 activated peptide-based prodrug might not be feasible due to poor stability of arginine containing peptides in plasma. However, the possibility remained that the introduction of a bulky hydrophobic moiety like an analog of thapsigargin might alter the relative rate of hK2 hydrolysis and/or stability in plasma. Therefore, we proceeded to synthesize a putative hK2-activated prodrug by coupling the GKAFRR peptide sequence (SEQ ID NO:9) to a primary amine containing TG analog. Previous studies had identified a potent amino acid containing TG analog [i.e. 8-O-(12[L-leucinoylamino]dodecanoyl)-8-O-debutanoylthapsigargin (L12ADT)] that was as cytotoxic as TG with an $LD_{50}$ value of ~30 nM against human prostate cancer cells in vitro (Jakobsen, C. M. et al. (2001) J. Med. Chem. 44:4696-4703). Previously, the L12ADT analog has been coupled to a PSA-specific peptide to produce a prodrug that is selectively cytotoxic to PSA-producing prostate cancer cells in vitro and in vivo (Denmeade, S. R. et al. (2003) J. Natl. Cancer Inst. 95:990-1000).

Figure 3:
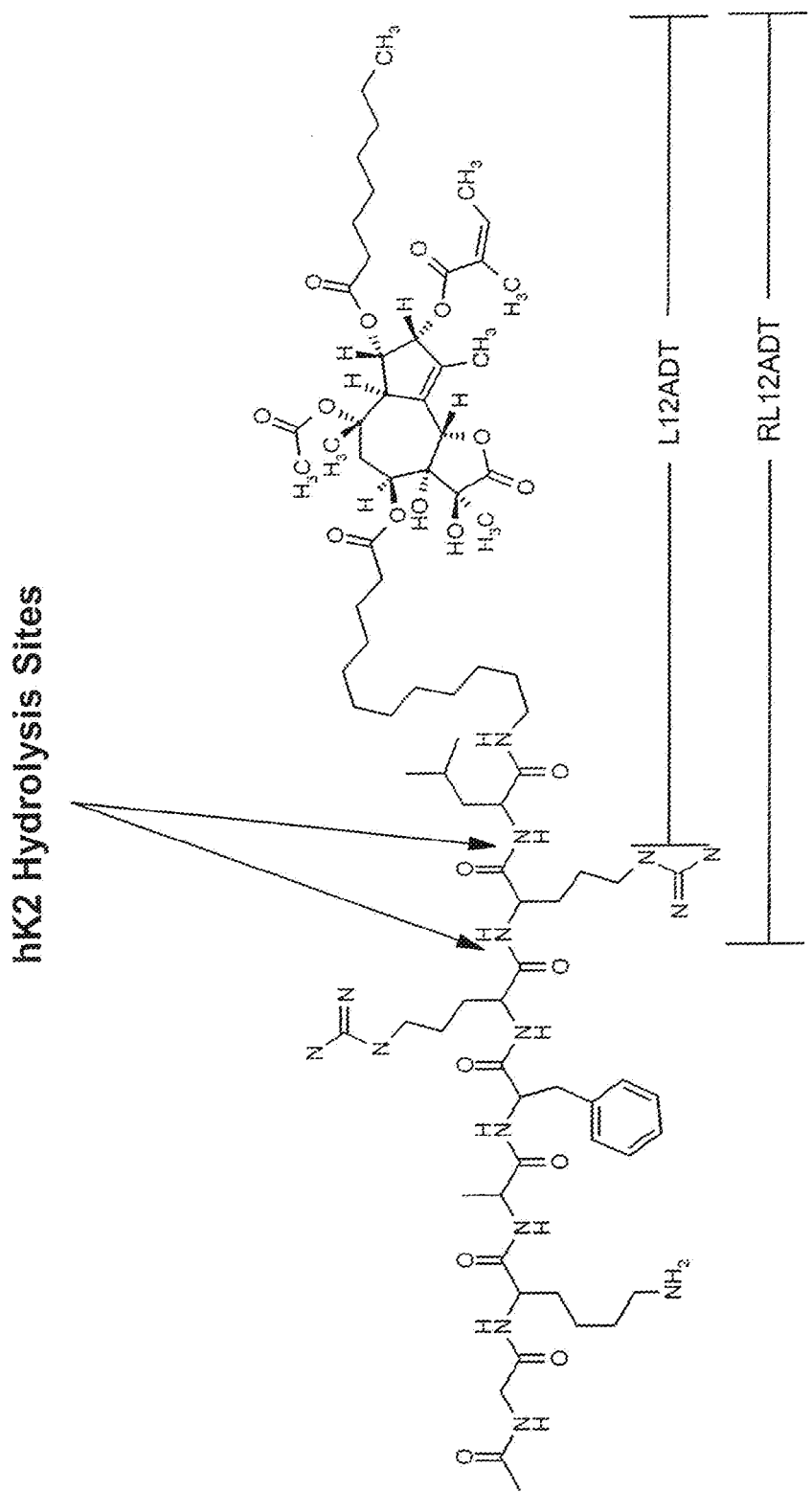
FIG. 3 depicts the chemical structure of the hK2 prodrug, Ac-GKAFRR-L12ADT. HK2 cleavage sites are indicated. The ratio of RL-12ADT:L-12ADT generated by hK2 digestion was 1:1.8.
Figure 4:
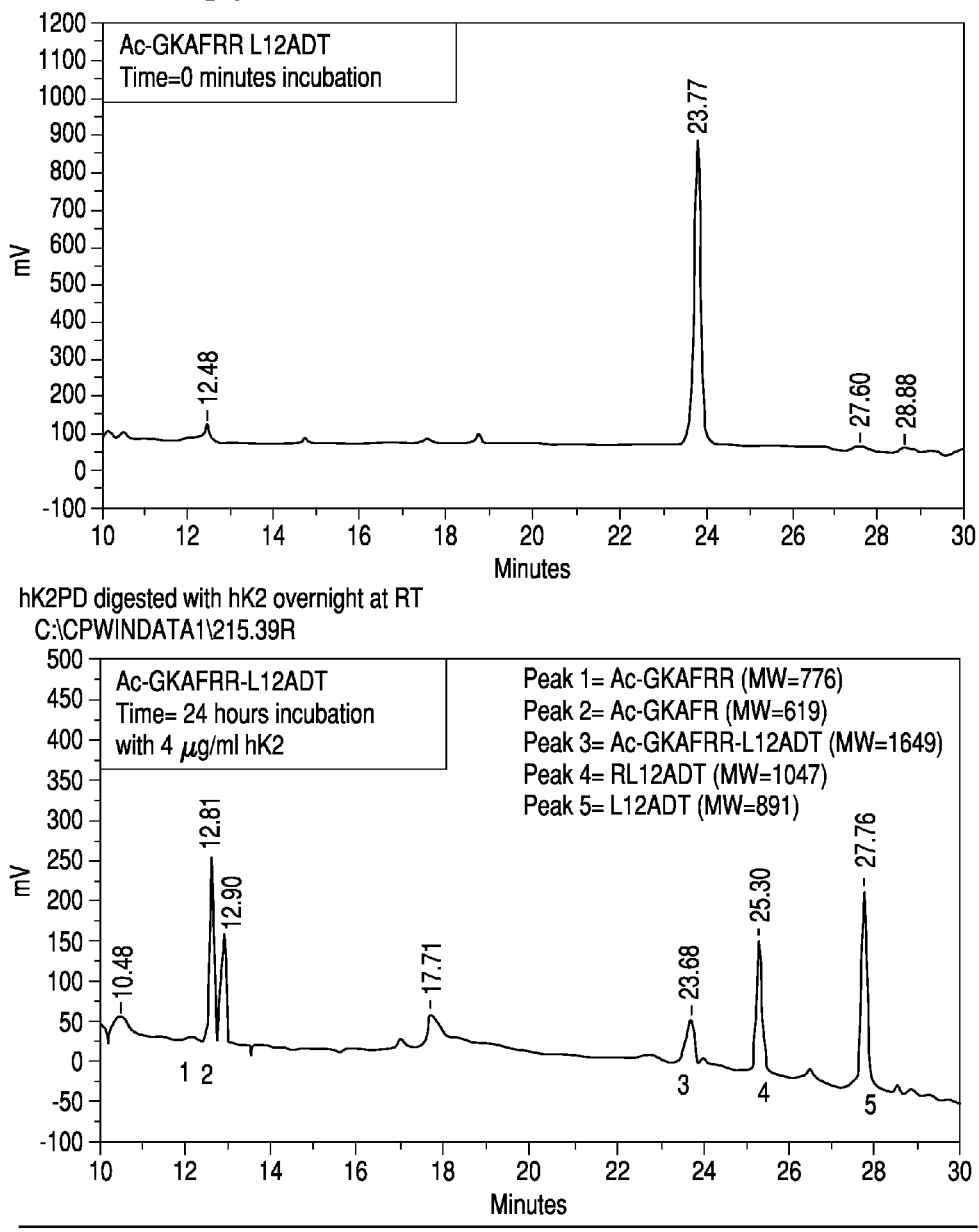
FIG. 4 depicts HPLC analysis of the hydrolysis of the hK2 prodrug Ac-GKAFRR-L12ADT by hK2 (4 µMg/ml) incubated in 50 mM Tris, 0.1 M NaCl, pH 7.8 at room temperature for 24 hours. The mass of each peak was confirmed by MALDI-TOF mass spectrometric analysis.

To synthesize an hK2 activated prodrug, the sequence C-terminal of the cleavage site (Dap-F-K') must be replaced by L12ADT and the N-terminal Y' replaced by an amino terminal acetyl group to produce a prodrug with the sequence ac-GKAFRR-L12ADT (FIG. 3). Prior to synthesizing the hK2 TG prodrug, it was essential to determine if hK2 could still effectively hydrolyze an acetylated peptide in which the Dap in P'1 position is replaced with leucine and where both the nitrotyrosine and lysine-ABZ were absent. Therefore the peptide Y'GKAFRRLGK' (SEQ ID NO:21) was synthesized to analyze the effect of substituting Dap in the P'1 position for leucine. Additionally a peptide ac-GKAFRRLG (SEQ ID NO:22) was synthesized to determine effects of acetylation and removal of Y' and K' on hK2 hydrolysis rates. Substitution of Dap-F with Leu-Gly resulted in only a modest decrease in hydrolysis rate (compare FIG. 2, triangles with FIG. 8, diamonds). In addition, HPLC analysis of hydrolysis of the non-fluorescence quenched acGKAFRR-LG peptide demonstrated that this peptide was rapidly hydrolyzed by hK2.

Figure 8:
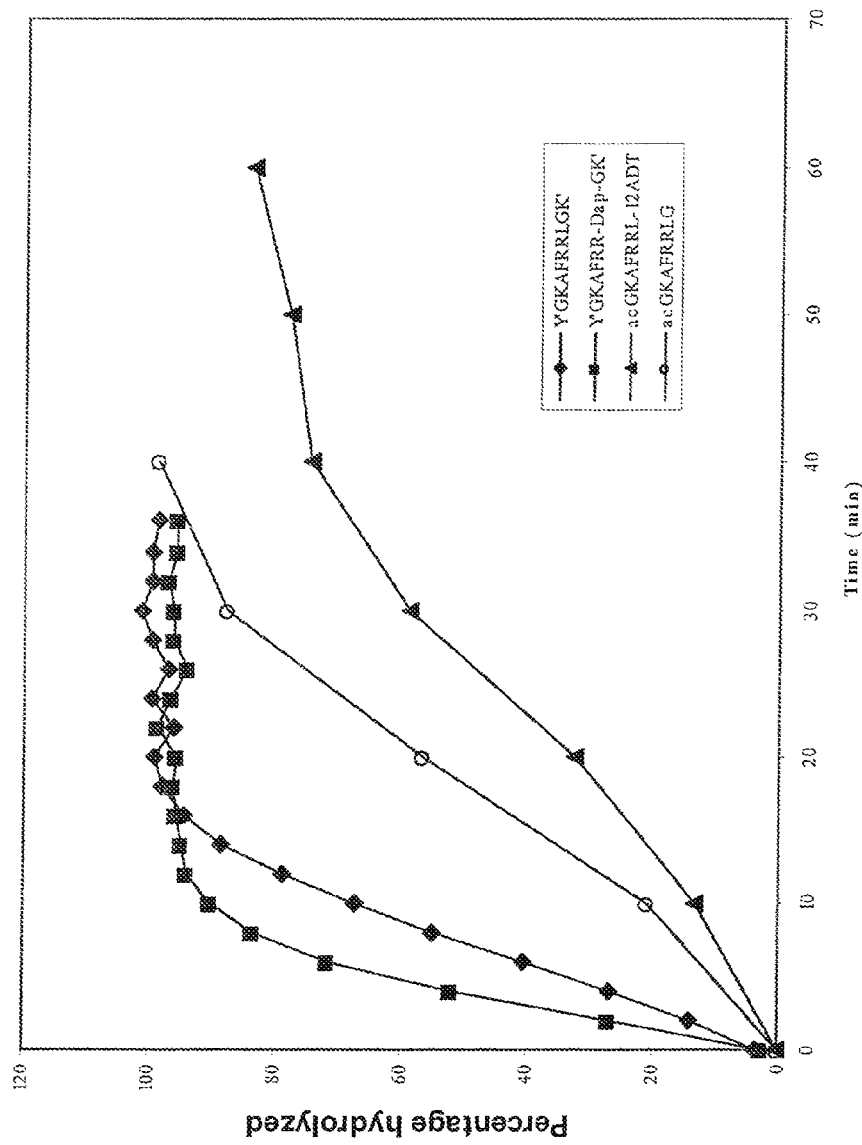
FIG. 8 depicts HK2 mediated hydrolysis of various peptide and prodrug substrates (125 mM each) (SEQ ID NOs:18, 41, 42 and 43). Fluorescent substrates were analyzed by means of a fluorescence plate-reader (ex=355 nm, em=460 nm). acGKAFRRL-12ADT (SEO ID NO:41) and acGKAFRRLG (SEQ ID NO:43) were analyzed by HPLC and quantified by HLPC integration.

On the basis of these results, ac-GKAFRR-L12ADT was synthesized. This putative hK2 prodrug was incubated with enzymatically active hK2 (4 µg/ml) to determine extent of hydrolysis over time. HPLC analysis of aliquots of the incubation mixture indicated that the hK2 prodrug is rapidly cleaved by hK2 (FIG. 8). MALDI-TOF analysis of the digestion products indicated that cleavage occurred after each arginine residue generating both Arg-Leu-12ADT (RL-12-ADT) and L-12ADT. In 25 min, 50% was hydrolyzed and after 1 hour, more than 80% of the starting prodrug was hydrolyzed. The ratio of the products RL-12ADT:L-12ADT was 1:1.8, as determined by HPLC integration.

Not unexpectedly, the time required to reach 50% hydrolysis is slightly longer for the L12ADT prodrug as compared to the peptide ac-GKAFRRLG (FIG. 8, crosses vs. triangles). This difference is most likely is due to substitution of the bulky, hydrophobic 12ADT moiety for the amino acids in the P'2 and P'3 position.

Figure 5:
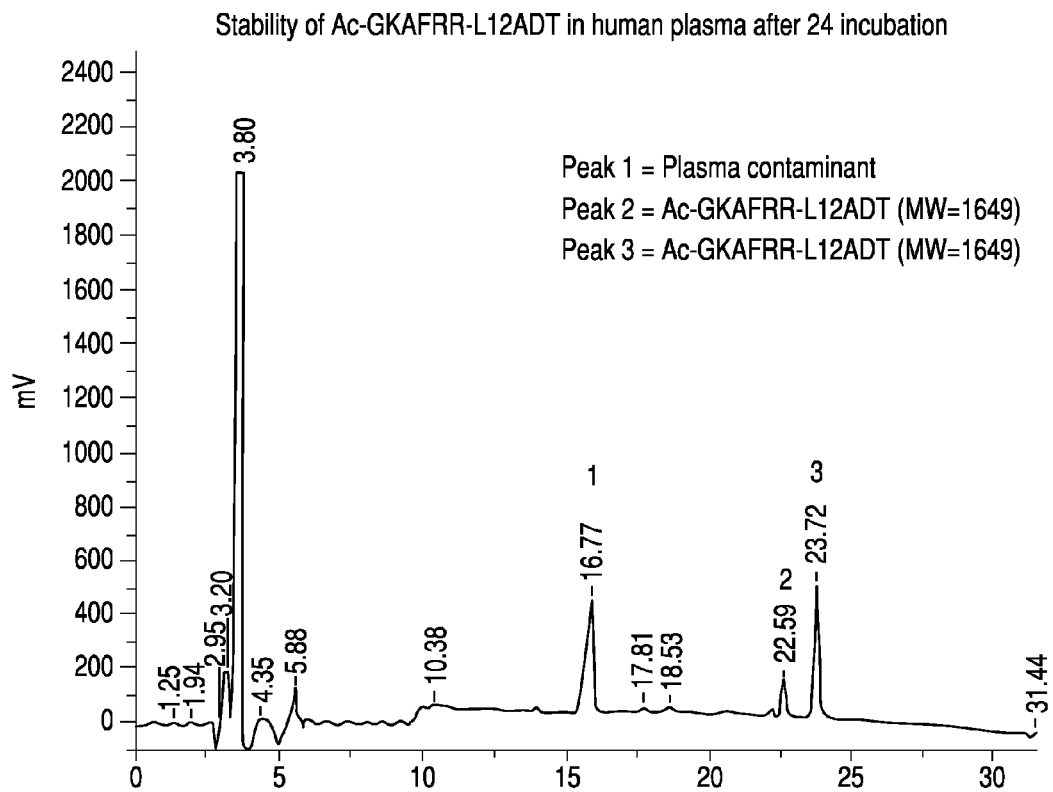
FIG. 5 depicts the stability of Ac-GKAFRR-L12ADT in human plasma after a 24 hour incubation, as determined by HPLC analysis. Ac-GKAFRR-L12ADT was incubated in 50% human plasma for 24 hours at room temperature. Peak 1 represents an unidentified plasma contaminant that was also present in control plasma. Peaks 2 and 3 both represent Ac-GKAFRR-L12ADT as confirmed by MALDI-TOF mass spectrometric analysis.

To determine the plasma stability for the hK2 prodrug, the prodrug was incubated in 50% fresh heparinized (1%) plasma for 24 hours at room temperature, precipitated the proteins by adding one volume of 1% TFA in acetonitrile and analyzed the supernatant by HPLC. Unexpectedly, HPLC analysis after 24 hrs incubation in plasma yielded only a single peak corresponding to the hK2 prodrug (FIG. 5). MALDI-TOF MS of the isolated single peak confirmed the stability of the molecule. No degradation products could be identified by both HPLC and MALDI-TOF analysis.

To determine whether merely the acetylation of the N-terminus of the hK2 prodrug contributed to its stability, an acetylated fluorescence-quenched peptide (ac-Y'GKAFRRLGK') was synthesized and compared its plasma stability with that of the non-acetylated peptide (Y'GKAFRRLGK'; SEQ ID NO:21). Surprisingly, hydrolysis of these two peptides was completely identical as judged from the generation of fluorescence in the plate-reader assay. Analytical HPLC indicated the same result. Evidently, acetylation of the N-terminus does not explain the difference in stability between the peptide and the peptide-drug conjugate. The paradoxical stability of the hK2 prodrug (ac-GKAFRR-L12ADT) compared to the peptide substrates may also be due to binding of the L12ADT moiety to plasma proteins that make it inaccessible to the plasma protease activity that is responsible for hydrolysis of unconjugated (and unbound) peptides.

Example 4

Pharmacokinetics and Toxicity Studies

Balb-C mice were treated in groups of 3 with a single intravenous injection of increasing doses of the ac-GKAFRR-L12ADT prodrug to establish the dose that killed 100% of mice (i.e. $LD_{100}$). In these studies the $LD_{100}$ was determined to be 11 μmoles/kg (i.e. 18.2 mg/kg). All mice, however, tolerated a single intravenous dose of 3.67 μmoles/kg and this dose was then used for further dosing and pharmacokinetic studies. An additional group of mice (n=8) received five consecutive daily intravenous injections with 3.67 μmoles/kg prodrug without any deaths or observable toxicity (i.e. weight loss <15% over baseline).

Figure 9:
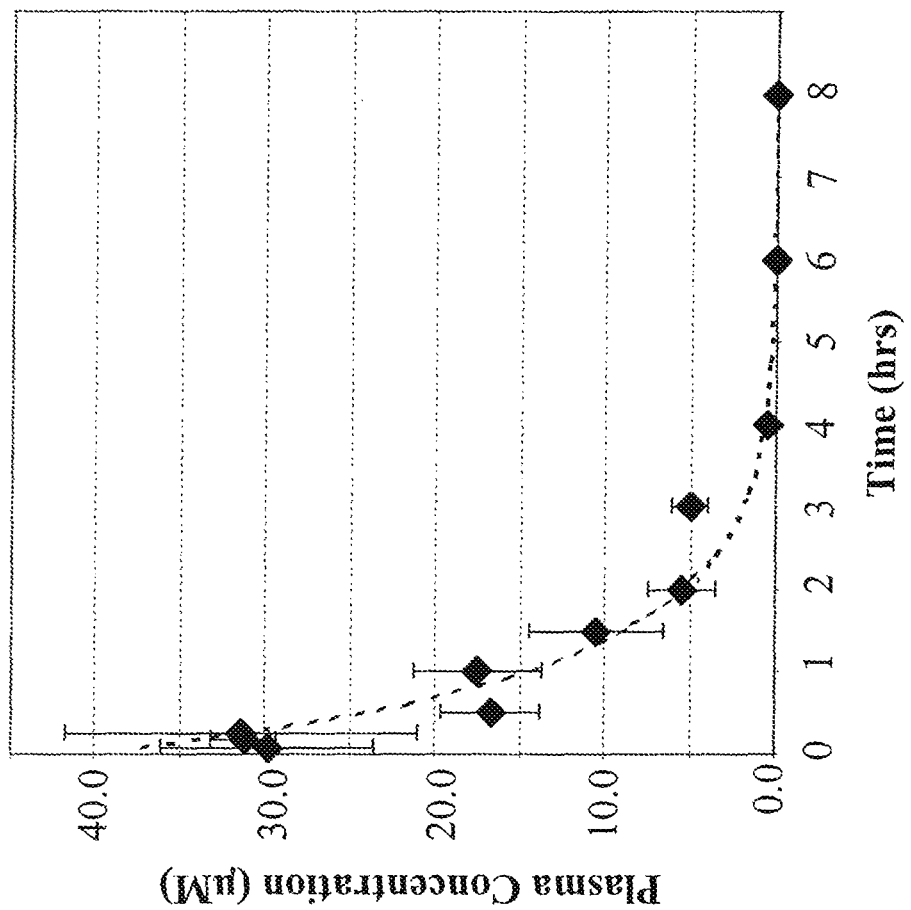
FIG. 9 depicts pharamcokinetic analysis of GKAFRR-L12ADT following single intravenous injection of 3.67 µmole/kg. Mice were treated in groups of 3 and then sacrificed at indicated time points. Data represent average ±standard error of plasma concentrations as determined by LC-MS analysis.

To determine pharmacokinetic parameters for the $hK_2$-activated thapsigargin prodrug, Balb-C mice (n=3/timepoint) were treated with a single intravenous dose of 3.67 μmmoles/kg of the ac-GKAFRR-L12ADT prodrug. At various time points (5, 10, 30 minutes and 1, 1.5, 2, 3, 4, 6, 12, 24 hrs) mice were sacrificed after blood was obtained by cardiac puncture. After precipitating serum proteins with acetonitrile, supernatants were evaluated by LC-MS to determine concentrations of ac-GKAFRR-L12ADT, R-L12ADT and L12ADT at each time points. Areas under the curve were converted to concentrations based on a standard curve that was linear for concentrations ranging from 1 nM to 10,000 nM. In this study, the Cmax occurred at 10 minutes post injection and was 36.8±7.2 μM (FIG. 9). The half-life of the prodrug was 40.7±1.2 minutes and the area under the curve was 2444.8±39.1 μmol*min/l (FIG. 9). Both RL12ADT and L12ADT were below the lower limit of detection (i.e. <1 nM) for all time points, FIG. 6. On the basis of these studies, we concluded that the ac-GKAFRR-L12ADT prodrug is highly stable to hydrolysis in the serum in vivo.

Example 6

Hydrolysis of hHK2 Peptide and Prodrug by Other Potential Tumor-associated Proteases Due to their short length, the hK2 peptide substrates could potentially be substrates for other trypsin-like proteases. Although a rather specific protease substrate can be defined with 7 amino acids, there is a lack of higher order structural information by which natural protein substrates normally impose high specificity. Cancer progression is often correlated with increased protease activity (Koblinski, J. E. et al. (2000) Clin. Chim. Acta 291:113-135). These activities could be potentially beneficial since they could broaden the scope of applications for protease activated prodrugs. To test the hypothesis that other tumor-associated proteases could activate the prodrug, a number of known proteases (table 3), implicated in cancer progression were selected to determine if our lead substrate, GKAFRRL (SEQ ID NO:22) could be efficiently hydrolyzed by any of these proteases. For this analysis, the trypsin-like serine proteases plasmin and urokinase and cathepsins B and D were selected. Hydrolysis of both the fluorescence quenched peptide substrate and the TG-prodrug was analyzed. No appreciable hydrolysis of either substrate was observed following incubation with Cathepsin D or Cathepsin B. Urokinase showed low activity on the fluorescence quenched peptide substrate, but not on the prodrug (Table I). Plasmin had a more than 10-fold slower rate of hydrolysis of the peptide substrate than hK2. However, with the prodrug, plasmin had an approximately 6-fold higher hydrolysis rate than hK2. Analysis of the cleavage products demonstrated that with plasmin, proteolysis occurs between the two arginines, generating the less potent cytotoxin Arg-Leu-12 ADT. Plasmin, therefore, could be a valid target for selective activation of the GKAFRR-L12ADT prodrug in other types of cancer where plasmin activation may play an important role.

TABLE I

Relative hydrolysis rates normalized to the enzyme with the lowest hydrolysis rate.

| Protease | Relative hydrolysis rate | |
|---|---|---|
| | Abz-GKAFRRLY' (SEQ ID NO: 54) | GKAFRRL12ADT hK2 prodrug (SEQ ID NO: 41) |
| Cathepsin D | 1 | 1 |
| Cathepsin B | 1 | 1 |
| Plasmin | 36 | 750 |
| hK2 | 353 | 125 |
| Urokinase | 17 | 1 |

Enzyme concentrations were 1 μg/ml.
Concentration of Abz-GKAFRRLY' was 500 μM, concentration hK2 prodrug (acGKAFRRL12ADT) was 100 μM.
A relative hydrolysis rate of 1 corresponds to approximately 0.1% digestion in 1 hour.

It is to be understood that while the invention has been described in conjunction with the detailed description thereof, the forgoing description is intended to illustrate and not limit the scope of the invention, which is defined by the scope of the appended claims. Other aspects, advantages, and modifications are within the scope of the following claims.

What is claimed is:

1. A method of treating prostate cancer, the method comprising
administering to a subject in need thereof a therapeutically effective amount of a prodrug comprising
a therapeutically active drug comprising the thapsigargin derivative 8-O-(12-[L-leucinoylamino]dodecanoyl)-8-O-debutanoylthapsigargin (L12ADT) and a peptide comprising an amino acid sequence having a cleavage site specific for an enzyme having a proteolytic activity of hK2,
wherein the peptide is linked to the therapeutically active drug to inhibit the therapeutic activity of the drug, and
wherein the peptide consists of the amino acid sequence G-K-A-F-R-R (SEQ ID NO: 9), and
wherein the therapeutically active drug is cleaved from the peptide upon proteolysis by an enzyme having a proteolytic activity of hK2.

2. The method of claim 1, wherein the peptide is linked directly to the therapeutic drug.

3. The method of claim 2, wherein the pepetide is linked directly to a primary amine group on the therapeutic drug.

4. The method of claim 1, wherein the peptide is linked to the therapeutic drug via a linker.

5. The method of claim 4, wherein the linker is an amino acid sequence.

6. The method of claim 5, wherein the linker comprises a leucine residue.

7. The method of claim 4, wherein the linker is selected from the group consisting of:

(a) CO—(CH=CH)$_{n1}$—(CH$_2$)$_{n2}$—Ar—NH$_2$,
(b) CO—(CH$_2$)$_{n2}$—(CH=CH)$_{n1}$—Ar—NH$_2$,
(c) CO—(CH$_2$)$_{n2}$—(CH=CH)$_{n1}$—CO—NH—Ar—NH$_2$,
(d) CO—(CH=CH)$_{n1}$—(CH$_2$)$_{n2}$—CO—NH—Ar—NH$_2$,
(e) CO—(CH$_2$)$_{n3}$—NH$_2$, and
(f) CO—(CH$_2$)$_{n3}$—NH—CO—CH(R$_4$)—NH$_2$, each of which is unsubstituted or alkyl-, aryl-, halo-, alkoxy-, alkenyl-, amido- or amino-substituted, and wherein n1 and n2 are from 0 to 5, n3 is from 0 to 15, Ar is any substituted or unsubstituted aryl group, attachment of NH$_2$ to Ar is in a ortho, meta or para position with respect to the remainder of the linker, and R$_4$ is any naturally occurring amino acid side chain.

* * * * *

SEQUENCE LISTING

<160> NUMBER OF SEQ ID NOS: 54

<210> SEQ ID NO 1
<211> LENGTH: 6

-continued

```
<212> TYPE: PRT
<213> ORGANISM: artificial sequence
<220> FEATURE:
<223> OTHER INFORMATION: synthetic peptide

<400> SEQUENCE: 1

Gly Lys Ala Arg Ala Phe
1               5

<210> SEQ ID NO 2
<211> LENGTH: 6
<212> TYPE: PRT
<213> ORGANISM: artificial sequence
<220> FEATURE:
<223> OTHER INFORMATION: synthetic peptide

<400> SEQUENCE: 2

Gly Lys Ala Val Arg Gln
1               5

<210> SEQ ID NO 3
<211> LENGTH: 6
<212> TYPE: PRT
<213> ORGANISM: artificial sequence
<220> FEATURE:
<223> OTHER INFORMATION: synthetic peptide

<400> SEQUENCE: 3

Gly Lys Ala Tyr Phe Met
1               5

<210> SEQ ID NO 4
<211> LENGTH: 6
<212> TYPE: PRT
<213> ORGANISM: artificial sequence
<220> FEATURE:
<223> OTHER INFORMATION: synthetic peptide

<400> SEQUENCE: 4

Gly Lys Ala Glu Lys Val
1               5

<210> SEQ ID NO 5
<211> LENGTH: 6
<212> TYPE: PRT
<213> ORGANISM: artificial sequence
<220> FEATURE:
<223> OTHER INFORMATION: synthetic peptide

<400> SEQUENCE: 5

Gly Lys Ala Phe Arg Lys
1               5

<210> SEQ ID NO 6
<211> LENGTH: 6
<212> TYPE: PRT
<213> ORGANISM: artificial sequence
<220> FEATURE:
<223> OTHER INFORMATION: synthetic peptide

<400> SEQUENCE: 6

Gly Lys Ala Lys Pro Arg
1               5

<210> SEQ ID NO 7
<211> LENGTH: 6
<212> TYPE: PRT
<213> ORGANISM: artificial sequence
```

```
<220> FEATURE:
<223> OTHER INFORMATION: synthetic peptide

<400> SEQUENCE: 7

Gly Lys Ala Ala Tyr Tyr
1               5

<210> SEQ ID NO 8
<211> LENGTH: 6
<212> TYPE: PRT
<213> ORGANISM: artificial sequence
<220> FEATURE:
<223> OTHER INFORMATION: synthetic peptide

<400> SEQUENCE: 8

Gly Lys Ala Trp Tyr His
1               5

<210> SEQ ID NO 9
<211> LENGTH: 6
<212> TYPE: PRT
<213> ORGANISM: artificial sequence
<220> FEATURE:
<223> OTHER INFORMATION: synthetic peptide

<400> SEQUENCE: 9

Gly Lys Ala Phe Arg Arg
1               5

<210> SEQ ID NO 10
<211> LENGTH: 6
<212> TYPE: PRT
<213> ORGANISM: artificial sequence
<220> FEATURE:
<223> OTHER INFORMATION: synthetic peptide

<400> SEQUENCE: 10

Gly Lys Ala Ile Gln Arg
1               5

<210> SEQ ID NO 11
<211> LENGTH: 6
<212> TYPE: PRT
<213> ORGANISM: artificial sequence
<220> FEATURE:
<223> OTHER INFORMATION: synthetic peptide

<400> SEQUENCE: 11

Gly Lys Ala Met Arg Gln
1               5

<210> SEQ ID NO 12
<211> LENGTH: 6
<212> TYPE: PRT
<213> ORGANISM: artificial sequence
<220> FEATURE:
<223> OTHER INFORMATION: synthetic peptide

<400> SEQUENCE: 12

Gly Lys Ala Ala Leu Met
1               5

<210> SEQ ID NO 13
<211> LENGTH: 6
<212> TYPE: PRT
<213> ORGANISM: artificial sequence
<220> FEATURE:
<223> OTHER INFORMATION: synthetic peptide
```

```
<400> SEQUENCE: 13

Gly Lys Ala Gln Gly Phe
1               5

<210> SEQ ID NO 14
<211> LENGTH: 6
<212> TYPE: PRT
<213> ORGANISM: artificial sequence
<220> FEATURE:
<223> OTHER INFORMATION: synthetic peptide

<400> SEQUENCE: 14

Gly Lys Ala Asn Met Asn
1               5

<210> SEQ ID NO 15
<211> LENGTH: 5
<212> TYPE: PRT
<213> ORGANISM: artificial sequence
<220> FEATURE:
<223> OTHER INFORMATION: synthetic peptide

<400> SEQUENCE: 15

Leu Ile Gln Ser Arg
1               5

<210> SEQ ID NO 16
<211> LENGTH: 5
<212> TYPE: PRT
<213> ORGANISM: artificial sequence
<220> FEATURE:
<223> OTHER INFORMATION: synthetic peptide

<400> SEQUENCE: 16

Asp Asp Asp Asp Lys
1               5

<210> SEQ ID NO 17
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: misc_feature
<222> LOCATION: (4)..(6)
<223> OTHER INFORMATION: X is any amino acid

<400> SEQUENCE: 17

Gly Lys Ala Xaa Xaa Xaa
1               5

<210> SEQ ID NO 18
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is acetylated 3-nitrotyrosine
<220> FEATURE:
<221> NAME/KEY: MISC_FEATURE
<222> LOCATION: (10)..(10)
<223> OTHER INFORMATION: X is 2-aminobenzoic acid-substituted lysine
      (Lys-Abz)

<400> SEQUENCE: 18
```

```
Xaa Gly Lys Ala Phe Arg Arg Leu Gly Xaa
1               5                   10

<210> SEQ ID NO 19
<211> LENGTH: 8
<212> TYPE: PRT
<213> ORGANISM: artificial sequence
<220> FEATURE:
<223> OTHER INFORMATION: synthetic peptide

<400> SEQUENCE: 19

Gly Ser Lys Gly His Phe Arg Leu
1               5

<210> SEQ ID NO 20
<211> LENGTH: 8
<212> TYPE: PRT
<213> ORGANISM: artificial sequence
<220> FEATURE:
<223> OTHER INFORMATION: synthetic peptide

<400> SEQUENCE: 20

Gly Ser Lys Gly His Phe His Leu
1               5

<210> SEQ ID NO 21
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MISC_FEATURE
<222> LOCATION: (10)..(10)
<223> OTHER INFORMATION: X is 2-aminobenzoic acid-substituted lysine
      (Lys-Abz)

<400> SEQUENCE: 21

Xaa Gly Lys Ala Phe Arg Arg Leu Gly Xaa
1               5                   10

<210> SEQ ID NO 22
<211> LENGTH: 7
<212> TYPE: PRT
<213> ORGANISM: artificial sequence
<220> FEATURE:
<223> OTHER INFORMATION: synthetic peptide

<400> SEQUENCE: 22

Gly Lys Ala Arg Ala Phe Leu
1               5

<210> SEQ ID NO 23
<211> LENGTH: 7
<212> TYPE: PRT
<213> ORGANISM: artificial sequence
<220> FEATURE:
<223> OTHER INFORMATION: synthetic peptide

<400> SEQUENCE: 23

Gly Lys Ala Val Arg Gln Leu
1               5

<210> SEQ ID NO 24
```

```
<211> LENGTH: 7
<212> TYPE: PRT
<213> ORGANISM: artificial sequence
<220> FEATURE:
<223> OTHER INFORMATION: synthetic peptide

<400> SEQUENCE: 24

Gly Lys Ala Tyr Phe Met Leu
1               5

<210> SEQ ID NO 25
<211> LENGTH: 7
<212> TYPE: PRT
<213> ORGANISM: artificial sequence
<220> FEATURE:
<223> OTHER INFORMATION: synthetic peptide

<400> SEQUENCE: 25

Gly Lys Ala Glu Lys Val Leu
1               5

<210> SEQ ID NO 26
<211> LENGTH: 7
<212> TYPE: PRT
<213> ORGANISM: artificial sequence
<220> FEATURE:
<223> OTHER INFORMATION: synthetic peptide

<400> SEQUENCE: 26

Gly Lys Ala Phe Arg Lys Leu
1               5

<210> SEQ ID NO 27
<211> LENGTH: 7
<212> TYPE: PRT
<213> ORGANISM: artificial sequence
<220> FEATURE:
<223> OTHER INFORMATION: synthetic peptide

<400> SEQUENCE: 27

Gly Lys Ala Lys Pro Arg Leu
1               5

<210> SEQ ID NO 28
<211> LENGTH: 7
<212> TYPE: PRT
<213> ORGANISM: artificial sequence
<220> FEATURE:
<223> OTHER INFORMATION: synthetic peptide

<400> SEQUENCE: 28

Gly Lys Ala Ala Tyr Tyr Leu
1               5

<210> SEQ ID NO 29
<211> LENGTH: 7
<212> TYPE: PRT
<213> ORGANISM: artificial sequence
<220> FEATURE:
<223> OTHER INFORMATION: synthetic peptide

<400> SEQUENCE: 29

Gly Lys Ala Trp Tyr His Leu
1               5

<210> SEQ ID NO 30
<211> LENGTH: 7
<212> TYPE: PRT
```

```
<213> ORGANISM: artificial sequence
<220> FEATURE:
<223> OTHER INFORMATION: synthetic peptide

<400> SEQUENCE: 30

Gly Lys Ala Phe Arg Arg Leu
1               5

<210> SEQ ID NO 31
<211> LENGTH: 7
<212> TYPE: PRT
<213> ORGANISM: artificial sequence
<220> FEATURE:
<223> OTHER INFORMATION: synthetic peptide

<400> SEQUENCE: 31

Gly Lys Ala Ile Gln Arg Leu
1               5

<210> SEQ ID NO 32
<211> LENGTH: 7
<212> TYPE: PRT
<213> ORGANISM: artificial sequence
<220> FEATURE:
<223> OTHER INFORMATION: synthetic peptide

<400> SEQUENCE: 32

Gly Lys Ala Met Arg Gln Leu
1               5

<210> SEQ ID NO 33
<211> LENGTH: 7
<212> TYPE: PRT
<213> ORGANISM: artificial sequence
<220> FEATURE:
<223> OTHER INFORMATION: synthetic peptide

<400> SEQUENCE: 33

Gly Lys Ala Ala Leu Met Leu
1               5

<210> SEQ ID NO 34
<211> LENGTH: 7
<212> TYPE: PRT
<213> ORGANISM: artificial sequence
<220> FEATURE:
<223> OTHER INFORMATION: synthetic peptide

<400> SEQUENCE: 34

Gly Lys Ala Gln Gly Phe Leu
1               5

<210> SEQ ID NO 35
<211> LENGTH: 7
<212> TYPE: PRT
<213> ORGANISM: artificial sequence
<220> FEATURE:
<223> OTHER INFORMATION: synthetic peptide

<400> SEQUENCE: 35

Gly Lys Ala Asn Met Asn Leu
1               5

<210> SEQ ID NO 36
<211> LENGTH: 10
<212> TYPE: PRT
<213> ORGANISM: artificial sequence
<220> FEATURE:
```

```
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substituted lysine
      (Lys-Abz)

<400> SEQUENCE: 36

Xaa Gly Lys Ala Arg Ala Phe Xaa Phe Xaa
1               5                   10

<210> SEQ ID NO 37
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substituted lysine
      (Lys-Abz)

<400> SEQUENCE: 37

Xaa Gly Lys Ala Lys Pro Arg Xaa Phe Xaa
1               5                   10

<210> SEQ ID NO 38
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substituted lysine
      (Lys-Abz)

<400> SEQUENCE: 38

Xaa Gly Lys Ala Phe Arg Arg Xaa Phe Xaa
1               5                   10

<210> SEQ ID NO 39
<211> LENGTH: 10
<212> TYPE: PRT
<213> ORGANISM: artificial sequence
<220> FEATURE:
<223> OTHER INFORMATION: synthetic peptide
<220> FEATURE:
```

```
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substituted Lysine
      (Lys-Abz)

<400> SEQUENCE: 39

Xaa Gly Lys Ala Met Arg Gln Xaa Phe Xaa
1               5                   10

<210> SEQ ID NO 40
<211> LENGTH: 12
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (10)..(10)
<223> OTHER INFORMATION: Dpr
<220> FEATURE:
<221> NAME/KEY: MISC_FEATURE
<222> LOCATION: (12)..(12)
<223> OTHER INFORMATION: X is 2-aminobenzoic acid substituted lysine
      (Lys-Abz)

<400> SEQUENCE: 40

Xaa Gly Ser Lys Gly His Phe Lys Leu Xaa Phe Xaa
1               5                   10

<210> SEQ ID NO 41
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (7)..(7)
<223> OTHER INFORMATION: X is leucine functionalized at the C-terminal
      end with 12ADT (L12ADT).

<400> SEQUENCE: 41

Gly Lys Ala Phe Arg Arg Xaa
1               5

<210> SEQ ID NO 42
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (8)..(8)
```

```
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substituted lysine
      (Lys-Abz)

<400> SEQUENCE: 42

Xaa Gly Lys Ala Phe Arg Arg Xaa Gly Xaa
1               5                   10

<210> SEQ ID NO 43
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION

<400> SEQUENCE: 43

Gly Lys Ala Phe Arg Arg Leu Gly
1               5

<210> SEQ ID NO 44
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (7)..(7)
<223> OTHER INFORMATION: X is leucine C-terminal functionalized with
      12ADT (L12ADT)

<400> SEQUENCE: 44

Gly Lys Ala Phe Arg Arg Xaa
1               5

<210> SEQ ID NO 45
<211> LENGTH: 11
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (10)..(10)
<223> OTHER INFORMATION: Dpr
<220> FEATURE:
<221> NAME/KEY: MISC_FEATURE
<222> LOCATION: (11)..(11)
<223> OTHER INFORMATION: X is 2-aminobenzoic acid-substituted lysine
      (Lys-Abz)

<400> SEQUENCE: 45

Xaa Gly Ser Lys Gly His Phe Lys Leu Xaa Xaa
1               5                   10

<210> SEQ ID NO 46
<211> LENGTH: 11
<212> TYPE: PRT
<213> ORGANISM: artificial sequence
<220> FEATURE:
<223> OTHER INFORMATION: synthetic peptide
```

```
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (10)..(10)
<223> OTHER INFORMATION: Dpr
<220> FEATURE:
<221> NAME/KEY: MISC_FEATURE
<222> LOCATION: (11)..(11)
<223> OTHER INFORMATION: X is 2-aminobenzoic acid-substituted lysine
      (Lys-Abz)

<400> SEQUENCE: 46

Xaa Gly Ser Lys Gly Pro Phe Lys Leu Xaa Xaa
1               5                   10

<210> SEQ ID NO 47
<211> LENGTH: 11
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (10)..(10)
<223> OTHER INFORMATION: Dpr
<220> FEATURE:
<221> NAME/KEY: MISC_FEATURE
<222> LOCATION: (11)..(11)
<223> OTHER INFORMATION: X is 2-aminobenzoic acid-substituted lysine
      (Lys-Abz)

<400> SEQUENCE: 47

Xaa Gly Ser Lys Gly His Phe His Leu Xaa Xaa
1               5                   10

<210> SEQ ID NO 48
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MISC_FEATURE
<222> LOCATION: (5)..(7)
<223> OTHER INFORMATION: X is any L-amino acid except cysteine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substitued lysine
      (Lys-Abz)

<400> SEQUENCE: 48

Xaa Gly Lys Ala Xaa Xaa Xaa Xaa Phe Xaa
1               5                   10

<210> SEQ ID NO 49
<211> LENGTH: 10
<212> TYPE: PRT
<213> ORGANISM: artificial sequence
```

```
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MISC_FEATURE
<222> LOCATION: (5)..(7)
<223> OTHER INFORMATION: X is any L-amino acid except cysteine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid substituted lysine
      bound to a solid phase PEGA support

<400> SEQUENCE: 49

Xaa Gly Lys Ala Xaa Xaa Xaa Xaa Phe Xaa
1               5                   10

<210> SEQ ID NO 50
<211> LENGTH: 6
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is any natural amino acid except cysteine
      protected with an FMOC group
<220> FEATURE:
<221> NAME/KEY: MISC_FEATURE
<222> LOCATION: (2)..(3)
<223> OTHER INFORMATION: X is any natural amino acid except cysteine
<220> FEATURE:
<221> NAME/KEY: MOD_RES
<222> LOCATION: (4)..(4)
<223> OTHER INFORMATION: Dpr
<220> FEATURE:
<221> NAME/KEY: MISC_FEATURE
<222> LOCATION: (6)..(6)
<223> OTHER INFORMATION: X is 2-aminobenzoic acid-substituted lysine
      (Lys-Abz) bound to a PEGA solid support

<400> SEQUENCE: 50

Xaa Xaa Xaa Xaa Phe Xaa
1               5

<210> SEQ ID NO 51
<211> LENGTH: 7
<212> TYPE: PRT
<213> ORGANISM: artificial sequence
<220> FEATURE:
<223> OTHER INFORMATION: synthetic peptide
<220> FEATURE:
<221> NAME/KEY: MOD_RES
<222> LOCATION: (1)..(1)
<223> OTHER INFORMATION: ACETYLATION
<220> FEATURE:
<221> NAME/KEY: MISC_FEATURE
<222> LOCATION: (2)..(2)
<223> OTHER INFORMATION: X is lysine protected with a side-chain ivDde
      protecting group

<400> SEQUENCE: 51

Gly Xaa Ala Phe Arg Arg Leu
1               5

<210> SEQ ID NO 52
```

```
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MISC_FEATURE
<222> LOCATION: (8)..(8)
<223> OTHER INFORMATION: X is 2-aminobenzoic acid substituted lysine
      (Lys-Abz) attached to a PEGA solid support

<400> SEQUENCE: 52

Xaa Gly Lys Ala Phe Arg Leu Xaa
1               5

<210> SEQ ID NO 53
<211> LENGTH: 10
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is 3-nitrotyrosine
<220> FEATURE:
<221> NAME/KEY: MOD_RES
<222> LOCATION: (8)..(8)
<223> OTHER INFORMATION: Dpr
<220> FEATURE:
<221> NAME/KEY: MISC_FEATURE
<222> LOCATION: (10)..(10)
<223> OTHER INFORMATION: X is 2-aminobenzoic acid-substituted lysine
      attached to a PEGA solid phase support

<400> SEQUENCE: 53

Xaa Gly Lys Ala Phe Arg Leu Xaa Phe Xaa
1               5                   10

<210> SEQ ID NO 54
<211> LENGTH: 8
<212> TYPE: PRT
<213> ORGANISM: artificial sequence
<220> FEATURE:
<223> OTHER INFORMATION: synthetic peptide
<220> FEATURE:
<221> NAME/KEY: MISC_FEATURE
<222> LOCATION: (1)..(1)
<223> OTHER INFORMATION: X is glycine N-terminal bound to a
      2-aminobenzoic acid group (Abz)
<220> FEATURE:
<221> NAME/KEY: MISC_FEATURE
<222> LOCATION: (8)..(8)
<223> OTHER INFORMATION: X is 3-nitrotyrosine

<400> SEQUENCE: 54

Xaa Lys Ala Phe Arg Arg Leu Xaa
1               5
```